United States Patent [19]

Lichenstein et al.

[11] Patent Number: 5,652,352
[45] Date of Patent: Jul. 29, 1997

[54] AFAMIN: A HUMAN SERUM ALBUMIN-LIKE GENE

[75] Inventors: Henri Stephen Lichenstein, Ventura; David Edwin Lyons, Thousand Oaks, both of Calif.; Mark Matsuo Wurfel, New York; Samuel Donald Wright, Larchmont, both of N.Y.

[73] Assignees: Amgen Inc., Thousand Oaks, Calif.; The Rockfeller University, New York, N.Y.

[21] Appl. No.: 222,619

[22] Filed: Mar. 31, 1994

[51] Int. Cl.$^6$ .......................... C07H 21/02; C07H 21/04; C12P 21/00
[52] U.S. Cl. .................. 536/23.5; 536/23.1; 435/69.1
[58] Field of Search .................. 435/6, 320.1, 69.1; 536/23.1, 23.5, 24.3, 23.2, 24.5; 514/44

[56] References Cited

FOREIGN PATENT DOCUMENTS 0353814  2/1990  European Pat. Off. .

OTHER PUBLICATIONS

Bélanger, L., et al., J. Biol. Chem., 269 (8):5481–5484 (1994).
Peters, Theodore ALBUMIN An Overview and Bibliography, Second Edition, 1992.
American Hospital Formulary Service Drug Information, "Blood Derivatives": 762–763 (1992).
Yamashita, T., et al., Biochem. Biophys. Res. Commun. 191 (2): 715–720 (1993).
Candish, John K., Pathology 25: 148–151 (1993).
Ohkawa, K., et al., Cancer Research 53: 4238–4242 (1993).
He, Xiao Min and Carter, Daniel C., Nature 358: 209–215 (1992).
Brown, J. M., et al., Inflammation, 13, (5): 583–589 (1989).
Emerson, T. E., Critical Medicine, 17 (7): 690–694 (1989).
Halliwell, Barry, Biochem. Pharmacol., 37 (4): 569–571 (1988).
Holt, M.E., et al., Br. J. exp. Path., 65: 231–241 (1984).
Suzuki, Y., et al., J. Clin. Invest., 90: 1530–1536 (1992).
Sakai, M., et al., J. Biol. Chem., 260 (8): 5055–5060 (1985).
Morinaga, T., et al., Proc. Natl. Acad. Sci. USA, 80: 4604–4608 (1983).
Lee, W. M., et al., Circulatory Shock, 28: 249–255 (1989).
Watt, G. H., et al., Circulatory Shock, 28: 279–291 (1989).
Williams, M. H., et al., Biochem. Biophys. Res. Commun. 153 (3): 1019–1024 (1988).
Yang, F., et al., Proc. Natl. Acad. Sci. USA, 82: 7994–7998 (1985).
Sommer et al. Nucleic Acid Res. 17: 6749 (1989).
Bennet, Science 271: 434 (1996).
Westermann et al, Biomed. Biochim. Acta. 48: 85–93.
Milligan et al, J. Med. Chem 36: 1923–1937 (1993).

*Primary Examiner*—Eggerton A. Campbell
*Attorney, Agent, or Firm*—Daniel R. Curry; Ron K. Levy; Steven M. Odre

[57] ABSTRACT

The invention relates to a novel human serum protein and nucleic acid referred to as AFM, which has one or more activities in common with human serum albumin, human a-fetoprotein, or human vitamin D binding protein and which has an apparent molecular weight by SDS-PAGE of 87 kd; variants thereof; and related genes, vectors, cells and methods.

12 Claims, 12 Drawing Sheets

FIG. 1A

```
CCCCGAGTCTCTGCGCCTTCACATAGTTGTCACAGGACTAAAGCAAATTGATCCAGGGGG      60
AAACACTGTAGACCGTGTATATAAAAACACTCTATAAACTGCAATGCTCAATTCTTAGTA    120
TAACTATTGTTGTTGTATTGATATTTATTAGTATTGGTGCTCACAAAAAGAGTCTAAATT    180
CCATAAGTCTTTATATTCAGGCTACTCTTTATTTTTGAAAACTCATTTTCTATCACCTTT    240
TTCTATTTTACTCCATATTGAGGCCTCATAAATCCAATTTTTTATTTCTTTCTTTTGTAA    300 m  k  l  l  k  l  t  g  f  i  f  f  l  f  f     -21
ATGTGGTTTCTACAAGATGAAACTACTAAAACTTACAGGTTTTATTTTTTTCTTGTTTT    360
                                              *
  l  t  e  s  l  t  L  P  T  Q  P  R  D  I  E  N  F  N  S  T     14
TTTTGACTGAATCCCTAACCCTGCCCACACAACCTCGGGATATAGAGAACTTCAATAGTA    420

Q  K  F  I  E  D  N  I  E  Y  I  T  I  I  A  F  A  Q  Y  V     34
CTCAAAAATTTATAGAAGATAATATTGAATACATCACCATCATTGCATTTGCTCAGTATG    480

Q  E  A  T  F  E  E  M  E  K  L  V  K  D  M  V  E  Y  K  D     54
TTCAGGAAGCAACCTTTGAAGAAATGGAAAAGCTGGTGAAAGACATGGTAGAATACAAAG    540

R  C  M  A  D  K  T  L  P  E  C  S  K  L  P  N  N  V  L  Q     74
ACAGATGTATGGCTGACAAGACGCTCCCAGAGTGTTCAAAATTACCTAATAATGTTTTAC    600
                                 *
  E  K  I  C  A  M  E  G  L  P  Q  K  H  N  F  S  H  C  C  S     94
AGGAAAAAATATGTGCTATGGAGGGGCTGCCACAAAAGCATAATTTCTCACACTGCTGCA    660

K  V  D  A  Q  R  R  L  C  F  F  Y  N  K  K  S  D  V  G  F    114
GTAAGGTTGATGCTCAAAGAAGACTCTGTTTCTTCTATAACAAGAAATCTGATGTGGGAT    720

L  P  P  F  P  T  L  D  P  E  E  K  C  Q  A  Y  E  S  N  R    134
TTCTGCCTCCTTTTCCCTACCCTGGATCCCGAAGAGAAATGCCAGGCTTATGAAAGTAACA    780

E  S  L  L  N  H  F  L  Y  E  V  A  R  R  N  P  F  V  F  A    154
GAGAATCCCTTTTAAATCACTTTTTATATGAAGTTGCCAGAAGGAACCCATTTGTCTTCG    840

P  T  L  L  T  V  A  V  H  F  E  E  V  A  K  S  C  C  E  E    174
CCCCTACACTTCTAACTGTTGCTGTTCATTTTGAGGAGGTGGCCAAATCATGTTGTGAAG    900

Q  N  K  V  N  C  L  Q  T  R  A  I  P  V  T  Q  Y  L  K  A    194
AACAAAACAAAGTCAACTGCCTTCAAACAAGGGCAATACCTGTCACACAATATTTAAAAG    960

F  S  S  Y  Q  K  H  V  C  G  A  L  L  K  F  G  T  K  V  V    214
CATTTTCTTCTTATCAAAAACATGTCTGTGGGGCACTTTTGAAATTTGGAACCAAAGTTG   1020

H  F  I  Y  I  A  I  L  S  Q  K  F  P  K  I  E  F  K  E  L    234
TACACTTTATATATATTGCGATACTCAGTCAAAAATTCCCCAAGATTGAATTTAAGGAGC   1080

I  S  L  V  E  D  V  S  S  N  Y  D  G  C  C  E  G  D  V  V    254
TTATTTCTCTTGTAGAAGATGTTTCTTCCAACTATGATGGATGCTGTGAAGGGGATGTTG   1140
```

FIG. 1B

```
       Q  C  I  R  D  T  S  K  V  M  N  H  I  C  S  K  Q  D  S  I      274
    TGCAGTGCATCCGTGACACGAGCAAGGTTATGAACCATATTTGTTCAAAACAAGATTCTA       1200

S  S  K  I  K  E  C  C  E  K  K  I  P  E  R  G  Q  C  I  I      294
    TCTCCAGCAAAATCAAAGAGTGCTGTGAAAAGAAAATACCAGAGCGCGGCCAGTGCATAA       1260

N  S  N  K  D  D  R  P  K  D  L  S  L  R  E  G  K  F  T  D      314
    TTAACTCAAACAAAGATGATAGACCAAAGGATTTATCTCTAAGAGAAGGAAAATTTACTG       1320

S  E  N  V  C  Q  E  R  D  A  D  P  D  T  F  F  A  K  F  T      334
    ACAGTGAAAATGTGTGTCAAGAACGAGATGCTGACCCAGACACCTTCTTTGCAAGTTTA       1380

F  E  Y  S  R  R  H  P  D  L  S  I  P  E  L  L  R  I  V  Q      354
    CTTTTGAATACTCAAGGAGACATCCAGACCTGTCTATACCAGAGCTTTTAAGAATTGTTC       1440

I  Y  K  D  L  L  R  N  C  C  N  T  E  N  P  P  G  C  Y  R      374
    AAATATACAAAGATCTCCTGAGAAATTGCTGCAACACAGAAAACCCTCCAGGTTGTTACC       1500
                        *

Y  A  E  D  K  F  N  E  T  T  E  K  S  L  K  M  V  Q  Q  E      394
    GTTACGCGGAAGACAAATTCAATGAGACAACTGAGAAAAGCCTCAAGATGGTACAACAAG      1560

C  K  H  F  Q  N  L  G  K  D  G  L  K  Y  H  Y  L  I  R  L      414
    AATGTAAACATTTCCAGAATTTGGGGAAGGATGGTTTGAAATACCATTACCTCATCAGGC      1620

T  K  I  A  P  Q  L  S  T  E  E  L  V  S  L  G  E  K  M  V      434
    TCACGAAGATAGCTCCCCAACTCTCCACTGAAGAACTGGTGTCTCTTGGCGAGAAAATGG      1680

T  A  F  T  T  C  C  T  L  S  E  E  F  A  C  V  D  N  L  A      454
    TGACAGCTTTCACTACTTGCTGTACGCTAAGTGAAGAGTTTGCCTGTGTTGATAATTTGG      1740
                            *

D  L  V  F  G  E  L  C  G  V  N  E  N  R  T  I  N  P  A  V      474
    CAGATTTAGTTTTTGGAGAGTTATGTGGAGTAAATGAAAATCGAACTATCAACCCTGCTG      1800

D  H  C  C  K  T  N  F  A  F  R  R  P  C  F  E  S  L  K  A      494
    TGGACCACTGCTGTAAAACAAACTTTGCCTTCAGAAGGCCCTGCTTTGAGAGTTTGAAAG      1860

D  K  T  Y  V  P  P  P  F  S  Q  D  L  F  T  F  H  A  D  M      514
    CTGATAAAACATATGTGCCTCCACCTTTCTCTCAAGATTTATTTACCTTTCACGCAGACA      1920

C  Q  S  Q  N  E  E  L  Q  R  K  T  D  R  F  L  V  N  L  V      534
    TGTGTCAATCTCAGAATGAGGAGCTTCAGAGGAAGACAGACAGGTTTCTTGTCAACTTAG      1980

K  L  K  H  E  L  T  D  E  E  L  Q  S  L  F  T  N  F  A  N      554
    TGAAGCTGAAGCATGAACTCACAGATGAAGAGCTGCAGTCTTTGTTTACAAATTTCGCAA      2040

V  V  D  K  C  C  K  A  E  S  P  E  V  C  F  N  E  E  S  P      574
    ATGTAGTGGATAAGTGCTGCAAAGCAGAGAGTCCTGAAGTCTGCTTTAATGAAGAGAGTC      2100
```

FIG. IC

```
      K   I   G   N                                                             578
CAAAAATTGGCAACTGAAGCCAGCTGCTGGAGATATGTAAAGAAAAAAGCACCAAAGGGA                   2160
AGGCTTCCTATCTGTGTGGTGATGAATCGCATTTCCTGAGAACAAAATAAAAGGATTTTT                   2220
CTGTAACTGTCACCTGAAATAATACATTGCAGCAAGCAATAAACACAACATTTTGTAAAG                   2280
TTAAAAA                                                                        2287
```

|  | % Similarity | | | |
|---|---|---|---|---|
|  | AFM | AFP | ALB | VDB |
| AFM |  | 60.4 | 54.8 | 41.2 |
| AFP | 39.6 |  | 59.1 | 40.9 |
| ALB | 35.6 | 40.2 |  | 45.8 |
| VDB | 20.7 | 21.2 | 24.4 |  |

% Identity (row axis label)

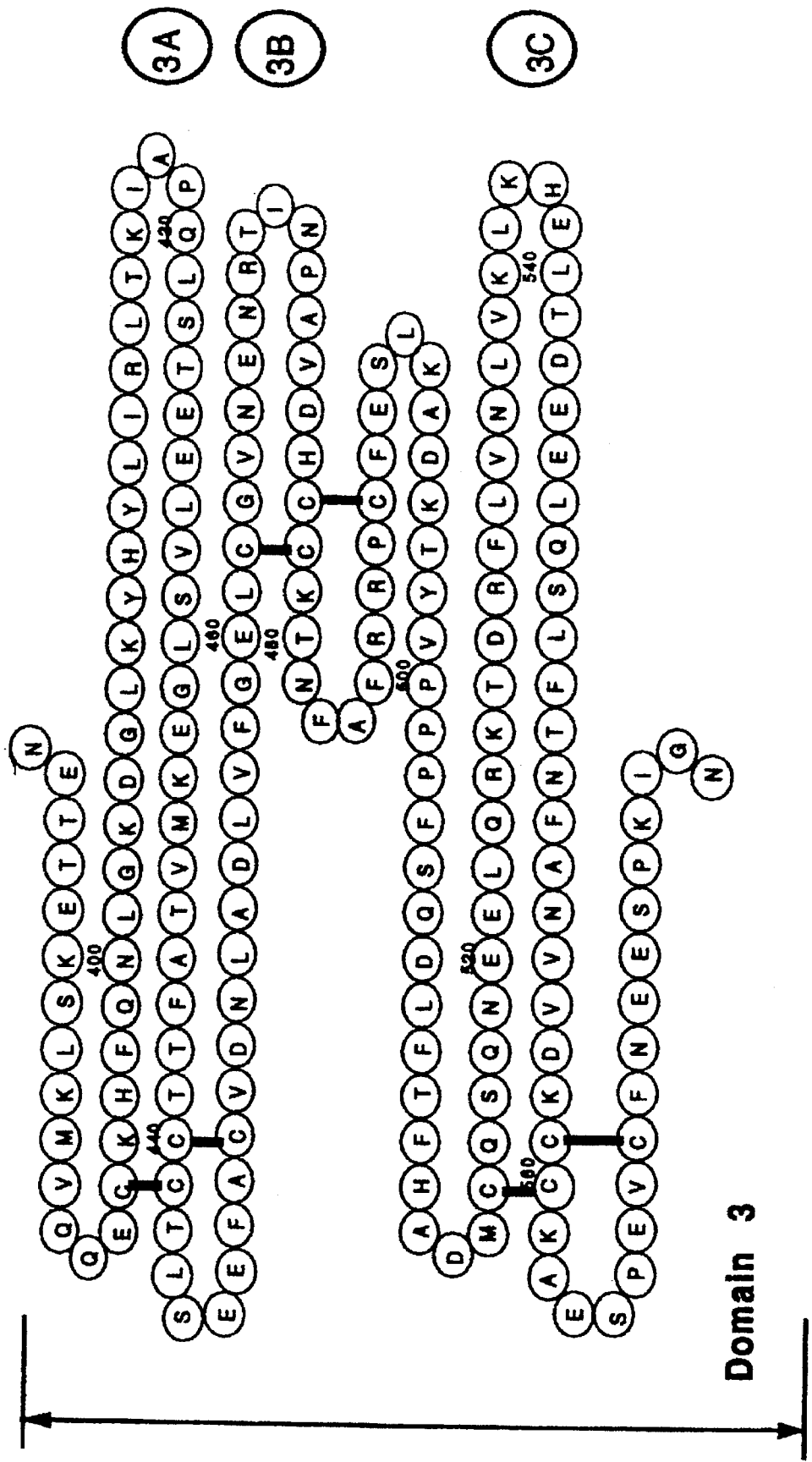

AFAMIN: A HUMAN SERUM ALBUMIN-LIKE GENE

FIELD OF THE INVENTION

Generally, the invention relates to the field of human serum proteins that are functionally and structurally similar to the related proteins: human serum albumin (ALB), human a-fetoprotein (AFP), and vitamin D-binding protein (VDB).

BACKGROUND OF THE INVENTION

The human serum proteins albumin (ALB), α-fete-protein (AFP) and vitamin D binding protein (VDB) are known to be members of a multigene ALB family. All three proteins are found in serum where they mediate the transport of a wide variety of ligands. ALB binds fatty acids, amine acids, steroids, glutathione, metals, bilirubin, lysolecithin, hematin, prostaglandins and pharmaceuticals (for review, see 1). AFP binds fatty acids, bilirubin and metals (2, 3). VDB binds vitamin D and its metabolites as well as fatty acids, actin, C5a and C5a des Arg (4-7).

In addition to their transport capabilities, ALB family proteins possess a wide assortment of other functional activities. ALB is the main contributor to the colloid oncotic pressure of plasma, acts as a scavenger of oxygen-free radicals and can inhibit copper-stimulated lipid peroxidation, hydrogen peroxide release, and neutrophil spreading (1, 8–10). AFP has been implicated in the regulation of immune processes (11–14) and VDB can act as a co-chemotactic factor for neutrophils (6, 15) and as an activating factor for macrophages (16).

The serum levels of ALB family proteins are also known to be responsive to various pathological conditions. ALB is a negative acute phase protein (17) whose levels decrease in times of stress. AFP levels are elevated in women carrying fetuses with certain developmental disorders (18, 19) and in individuals with hepatocarcinoma, teratocarcinoma, hereditary tyrosinemia or ataxia-telangiectasia (20-24). VDB levels are decreased in patients with septic shock (25) or fulminant hepatic necrosis (26, 27).

ALB family members also have significant structural similarities. Homology has been observed at the primary amino acid sequence level and there is also a well-conserved pattern of Cys residues which predicts similar secondary structures (28–32). ALB family genes have similar exon/intron organizations (33–36) and all have been mapped to human chromosome 4 within the region 4q11–q22 (37, 38).

Human "Afamin" (abbreviated as "AFM") is a novel serum protein with a molecular weight of 87000 daltons. It shares strong similarity to albumin family members and has the characteristic pattern of disulfide bonds observed in this family. In addition, the gene maps to chromosome 4 as do other members of the albumin gene family. Thus, AFM is the fourth member of the albumin family of proteins. AFM cDNA was stably transfected into Chinese hamster ovary cells and recombinant protein (rAFM) was purified from conditioned medium. Both rAFM and AFM purified from human serum react with a polyclonal antibody that was raised against a synthetic peptide derived from the deduced amino acid sequence of AFM. It is expected that AFM will have properties and biological activities in common with ALB, AFP, and VDB.

Publications relating to "Background of the Invention"

1. Peters, T. Jr., Adv. Protein Chem. 37, 161–245 (1985).
2. Parmelee, D. C., Evenson, M. A., and Deutsch, H. F. J. Biol. Chem. 253, 2114–2119 (1978).
3. Berde, C. B., Nagai, M., Deutsch, H. F., J. Biol. Chem. 254, 12609–12614 (1979).
4. Daiger, S. P., Schanfield, M. S., and Cavalli-Sforza, L. L., Proc. Nat. Acad. Sci. U.S.A. 72, 2076–2080 (1975).
5. Van Baelen, H., Bouillon, R., and De Moor, P., J. Biol. Chem. 255, 2270–2272 (1980).
6. Kew, R. R., and Webster, R. O., J. Clin. Invest. 82, 364–369 (1988).
7. Williams, M. H., Van Alstyne, E. L., and Galbraith, R. M., Biochem. Bipophys. Res. Commun. 153, 1019–1024 (1988).
8. Holt, M. E., Ryall, M. E. T., and Campbell, A. K., Br. J. exp. Path. 65, 231–241 (1948).
9. Gutteridge, J. M. C., Biochim. Biophys ACTA 869, 119–127 (1986).
10. Nathan, C., Xie, Q-W., Halbwachs-Mecarelli, L. and Jin, W. W., J. Cell Biol. 122, 243–256 (1993).
11. Yachnin, S., Proc. Natl. Acad. Sci. U.S.A. 73, 2857–2861 (1976).
12. Auer, I. O., and Kress, H. G., Cell. Immunol. 30, 173–179 (1977).
13. Alpert, E., Dienstag, J. L., Sepersky, S., Littman, B., and Rocklin, R., Immunol.Commun. 7, 163–185 (1978).
14. Chakraborty, M., and Mandal, C., Immunol. Invest. 22, 329–339 (1993).
15. Perez, H. D., Kelly, E., Chenoweth, D., and Elfman, F., J. Clin. Invest. 82, 360–363 (1988).
16. Yamamoto, N. and Homma, S., Proc. Natl. Acad. Sci. U.S.A. 88, 8539–8543 (1991).
17. Koj, A., in The Acute Phase Response to Injury and Infection 1 (Gordon, A. H., and Koj, A. eds) pp. 45–160 (1985).
18. Brock, D. J. H., and Sutcliffe, R. G., Lancet 2, 197–199 (1972).
19. Allan, L. D., Ferguson-Smith, M. A., Donald, I., Sweet, E. M. and Gibson, A. A. M., Lancet 2 522–525 (1973).
20. Waldmann, T. A., and McIntire, K. R., Lancet 2, 1112–1115 (1972).
21. Belanger, L., Belanger, M., Prive, L., Larochelle, J., Tremblay, M., and Aubin, G., Pathol. Biol. 21, 449–455 (1973).
22. Belanger, L., Pathol. Biol. 21, 457–463 (1973).
23. Ruoslahti, E., Pihto, H., and Seppala, M., Transplant. Rev. 20, 38–60 (1974).
24. Tamaoki, T., and Fausto, in Recombinant DNA and Cell Proliferation (Stein G. and Stein J. eds.) pp. 145–168 (1984).
25. Lee, W. M., Reines, D., Watt, G. H., Cook, J. A., Wise, W. C., Halushka, P. V., and Galbraith, R. M., Circ. Shock. 28, 249–255 (1989).
26. Young, W. O., Goldschmidt-Clermont, P. J., Emerson, D. L., Lee, W. M., Jollow, D. J., and Galbraith, R. M., Lab. Clin. Med. 110, 83–90 (1987).
27. Goldschmidt-Clermont, P. J., Lee, W. M., and Galbraith, R. M., Gastroenterology 94, 1454–1458 (1988).
28. Lawn, R. M., Adelman, J., Bock, S. C., Franke, A. E., Houck, C. M., Najarian, R. C., Seeburg, P. H., and Wion, K. L., Nucleic Acid Res. 9, 6103–6114 (1981).
29. Dugaiczyk, A., Law, S. W., and Dennison, O. E., Proc. Natl. Acad. Sci. U.S.A. 79, 71–75 (1982).
30. Morinaga, T., Sakai, M., Wegmann, T. G., and Tamaoki, T., Proc. Natl. Acad. Sci. U.S.A. 80, 4604–4608 (1983).
31. Cooke, N. E. and David, E. V., J. Clin. Invest. 76, 2420–2424 (1985).
32. Yang, F., Brune, J. L., Naylor, S. L., Cupples, R. L., Naberhaus, K. H., and Bowman, B. H., Proc. Natl. Acad. Sci. U.S.A. 82, 7994–7998 (1985).
33. Sakai, M., Morinaga, T., Urano, Y., Watanabe, K., Wegmann, T. G., and Tamaoki, T., J. Biol. Chem. 260, 5055–5060 (1985).

34. Minghetti, P. P., Ruffner, D. E., Kuang, W-J., Dennison, O. E., Hawkins, J. W., Beattie, W. G., and Dugaiczyk, A., *J. Biol. Chem.* 261, 6747–6757 (1986).

35. Gibbs, P. E. M., Zielinski, R., Boyd, C., and Dugaiczyk, A., *Biochemistry* 26, 1332–1343 (1987).

36. Witke, W. F., Gibbs, P. E. M., Zielinski, R., Yang, F., Bowman, B. H., and Dugaiczyk, A., *Genomics* 16, 751–754 (1993).

37. Mikkelsen, M., Jacobsen, P. and Henningsen, K., *Hum. Hered.* 27, 105–107 (1977).

38. Harper, M. E., and Dugaiczyk, A., *Am. J. Hum. Genet.* 35, 565–572 (1983).

The sections below contain a summary of background information that is currently available on ALB, AFP, and VDB and contains lists of additional publications relating to these known proteins.

I. Human Serum Albumin

Human serum albumin is an important factor in the regulation of plasma volume and tissue fluid balance through its contribution to the colloid osmotic pressure of plasma. Albumin normally constitutes 50–60% of plasma proteins and because of its relatively low molecular weight (66,300–69,000), exerts 80–85% of the colloidal osmotic pressure of the blood.

The best known functions of ALB involve regulation of transvascular fluid flux and hence, intra and extravascular fluid volumes and transport of lipid and lipid-soluble substances. ALB solutions are frequently used for plasma volume expansion and maintenance of cardiac output in the treatment of certain types of shock or impending shock including those resulting from burns, surgery, hemorrhage, or other trauma or conditions in which a circulatory volume deficit is present. Transfusions of whole blood or red blood cells also may be necessary, depending on the severity of red blood cell loss.

Intravenous (IV) administration of concentrated ALB solutions causes a shift of fluid from the interstitial spaces into the circulation and a slight increase in the concentration of plasma proteins. When administered IV to a well-hydrated patient, each volume of 25% ALB solution draws about 3.5 volumes of additional fluid into the circulation within 15 minutes, reducing hemoconcentration and blood viscosity. In patients with reduced circulating blood volumes (as from hemorrhage or loss of fluid through exudates or into extravascular spaces), hemodilution persists for many hours, but in patients with normal blood volume, excess fluid and protein are lost from the circulation within a few hours. In dehydrated patients, ALB generally produces little or no clinical improvement unless additional fluids are administered.

Although ALB contains some bound amino acids, it provides only modest nutritive effect. ALB binds and functions as a carrier of intermediate metabolites (including bilirubin), trace metals, some drugs, dyes, fatty acids, hormones, and enzymes, thus affecting the transport, inactivation, and/or exchange of tissue products.

ALB is also involved in a number of other vital functions, some of which have only recently been suggested and perhaps others which are as yet unrecognized. Among recognized unique features of albumin are: a) binding, and hence, inactivation of toxic products; b) regulation of the plasma and interstitial fluid concentrations of endogenous and exogenously administered substances and drugs; c) involvement in anticoagulation; d) maintenance of microvascular permeability to protein; and e) scavenging of free radicals and prevention of lipid peroxidation. This latter property may prove to be critically important, particularly in inflammatory disease states in which free radicals are thought to be a major culprit in direct damage due to tissue oxidation, and indirect tissue damage due to inactivation of important antiproteinases such as $a_1$-PI and AT-III.

The following is a more detailed summary of the many uses for ALB that have been reported in the literature:

A. Functions of ALB

Contributes to colloid osmotic pressure and thus prevents water loss from circulation;

Aids in transport, distribution, metabolism of fatty acids (primarily long chain), amino acids (Cys and Trp), steroids, glutathione, metals (Ca, Zn), bilirubin, lysolecithin, hematin, prostaglandins and pharmaceuticals to liver, intestine, kidney and brain presumably through specific albumin receptors that have been identified on the endothelium;

Serves as a reservoir for fatty acids intra and extravascularly (60% of the ALB is found extravascularly);

Modification of doxorubicin (DXR) by conjugating it to bovine serum albumin (BSA) improved chemotherapeutic efficiency of DXR presumably by decreasing efflux of BSA-DXR compared to DXR alone (in animal models), suggesting a similar use with ALB;

Inhibits Cu-stimulated lipid peroxidation and hemolysis of erythrocyte membranes (acts as antioxidant);

Scavenges HOCl and peroxy radicals;

Prevents peroxidation of fatty acids by binding to them;

May exert a protective effect in body fluids that have little endogenous antioxidant protection (e.g., eye and cerobrospinal fluids);

In urine, high levels of ALB are diagnostic for detection of early renal pathology in diabetics;

Administered to combat shock and given to neonates with respiratory distress syndrome;

Administered as a vehicle for hematin to treat acute intermittent porphyria;

Used in tissue culture in place of whole serum;

Enhances effectiveness of superoxide dismutase (SOD) when coupled to SOD through enhanced serum half-life;

In microsphere form, ALB is useful as a carrier of therapeutic agents;

Inhibits hydrogen peroxide release and neutrophil spreading.

B. publications relating to ALB

38. Peters, Theodore in *ALBUMIN An Overview and Bibliography*, Second Edition, 1992.

39. American Hospital Formulary Service Drug Information, *Blood Derivatives*, 762–763 (1992).

40. Yamashita, T., et al., *Biochem. Biophys. Res. Commun.* 191 (2), 715–720 (1993).

41. Candlish, John K., *Pathology* 25, 148–151 (1993).

42. Ohkawa, K., et al., *Cancer Research* 54, 4238–4242 (1993).

43. He, Xiao Min and Carter, Daniel C., *Nature* 358, 209–215 (1992).

44. Brown, J. M., et al., *Inflammation* 13 (5), 583–589 (1989).

45. Emerson, T. E., *Critical Care Medicine* 17 (7), 690–694 (1989).

46. Halliwell, Barry, *Biochem. Pharmacol.* 37 (4), 569–571 (1988).

47. Holt, M. E., et al., Br. *J. Exp. Path.* 65, 231–241 (1984).

II. Alpha Fetoprotein

Alpha-fetoprotein (AFP; molecular weight 70,000) is a major serum protein produced during development and is produced primarily by the fetal liver and yolk sac cells. Its synthesis decreases markedly after birth and only trace amounts are present in the serum of adults. Increased adult serum levels are a sign of hepatoma or yolk sac tumor, since these tumors produce AFP. The specific associations of AFP with fetal development as well as the above type of malignancies has attracted much interest and many studies have been done on the structure of AFP and its gene, the regulation of gene expression, and biological functions.

Similar to ALB, AFP has been shown to bind various ligands such as unsaturated fatty acids, estrogens, bilirubin, copper and nickel ions, and others. AFP also has been claimed to regulate immune processes in a variety of systems from many different laboratories, although the results are controversial.

The following is a more detailed list of uses for AFP that are available in the literature:

A. Functions of AFP

Binds unsaturated fatty acids, estrogens, bilirubin, Cu, Ni;

Elevated levels in amniotic fluid of pregnant women indicative of fetal malformations;

High levels also found in hereditary tyrosinemia and ataxia-telangiectasia (autosomal recessive disorder characterized by a defect in tissue differentiation of thymus and liver);

Inhibits NK cell activity;

Induces T suppressor cells;

Inhibits mitogenic responses of lymphocytes to PHA and ConA;

Inhibits T cell proliferation to Ia determinants;

Decreases macrophage phagocytosis and Ia expression;

Inhibits FSH-mediated estradiol production by porcine granulosa cells;

Enhances growth-factor mediated cell proliferation of porcine granulosa cells.

B. Publications relating to AFP

48. Suzuki, Y., et al., *J. Clin. Invest.* 90, 1530–1536 (1992).
49. Sakai, M., et al., *J. Biol. Chem.* 260 (8), 5055–5060 (1985).
50. EPO Patent Application No. 0353814, Feb. 7, 1990.

III. Vitamin-D Binding Protein

The group-specific component (Gc; VDB) is an $a_2$-globulin of molecular weight 51,000. It is synthesized in the liver and is the major vitamin D-binding protein in plasma. VDB appears in human populations as three common genetic phenotypes: Gc1, Gc2, and Gc2-1. VDB has also been reported to bind G-actin and to be spatially associated with IgG on lymphocyte membranes.

The following is a more detailed list of uses for VDB that are available in the literature:

A. Functions of VDB

Binds seco-steroid, vitamin D and the derivatives 25-hydroxy vitamin D and 1,25 hydroxy vitamin D, possibly for transport in plasma;

1,25 vitamin D can differentiate monocytes and VDB prevents this;

Binds actin (prevents assembly of actin polymers);

Binds unsaturated fatty acids (e.g., arachidonic acid);

Binds C5a and C5a des Arg to act as a cochemotactic factor for neutrophils;

Acts as an activating factor for macrophages.

B. Publication relating to VDB

51. Watt, G. H., et al., *Circulatory Shock* 28, 279–291 (1989).

The protein of the present invention, AFM, bears a strong similarity in structure to ALB, AFP, and VDB, and is therefore expected to share the above utilities and activities with the known proteins discussed above.

SUMMARY OF THE INVENTION

In the course of experiments designed to purify a serum protein which could inhibit the binding of lipopolysaccharide (LPS)-coated erythrocytes to human macrophages, the inventors purified a novel human protein that co-purifies with apolipoprotein A1 (ApoA1). The novel protein has an apparent molecular weight of 87,000 when run on SDS-PAGE and is designated as AFM. Herein, the inventors describe the cloning of the cDNA for AFM and demonstrate that AFM has a striking similarity, both structurally and functionally, to other members of the ALB family. In addition, the inventors purified AFM from the serum-free conditioned medium of CHO D⁻ cells transfected with the cDNA for AFM, thus allowing the study of AFM in the absence of ApoA1.

Based on the above, the present invention provides purified and isolated polynucleotides (e.g., DNA sequences and RNA transcripts thereof) encoding a novel human polypeptide, "AFM" as well as complexes of AFM with ApoA1 and/or lipids, and polypeptide variants (including fragments and analogs) thereof which display one or more biological activities or properties specific to AFM.

Preferred DNA sequences of the invention include genomic and cDNA sequences as well as wholly or partially chemically and or enzymatically synthesized DNA sequences and biological replicas thereof. Also provided are autonomously replicating recombinant constructions such as plasmid and vital DNA vectors incorporating such sequences and especially vectors, wherein DNA encoding AFM or an AFM variant are operatively linked to an endogenous or exogenous expression control DNA sequence.

According to another aspect of the invention, host cells, especially unicellular host cells such as prokaryotic and eukaryotic cells, are stably transformed with DNA sequences of the invention in a manner allowing AFM and variants thereof to be expressed therein.

Host cells of the invention are useful in methods for the large scale production of AFM and AFM variants wherein the cells are grown in a suitable culture medium and the desired polypeptide products are isolated from the cells or from the growth medium.

Novel AFM and AFM variant products of the invention may be obtained as isolates from natural cell sources, but are preferably produced by recombinant procedures involving host cells of the invention. The products may be obtained in fully or partially glycosylated, partially or wholly deglycosylated, or non-glycosylated forms, depending on the host cell selected for recombinant production and/or post-isolation processing. The products may also be bound to other molecules, such as cellularly derived lipids and/or ApoA1.

Products of the invention include monomeric and multimeric polypeptides having the sequence of amino acid residues numbered −21 through 578 nucleotides 318–2114 and 381–2114 as set out in FIG. 1 herein. As explained in detail infra, this sequence includes a putative signal or leader sequence which precedes the "mature" protein sequence and spans residue −21 (Met) through residue −1 (Thr) followed by the mature protein spanning residues 1 (Leu) to residue 578 (Asn). Based on amino acid composition, the calculated molecular weight of the mature protein lacking glycosylation or other post-translational modification is approximately 66,576 daltons.

AFM variants of the invention may comprise fragments including one or more of the regions specified herein and may also comprise polypeptide analogs wherein one or more of the specified amino acids is deleted or replaced: (1) without substantial loss, and preferably with enhancement, of one or more biological activities or immunological characteristics specific for AFM; or (2) with specific modulation of a particular ligand/receptor binding function. Analog polypeptides including additional amino acid residues (e.g., lysine) that facilitate multimer formation are also contemplated.

Further comprehended by the present invention are antibodies (e.g., monoclonal and polyclonal antibodies, single chain antibodies, chimeric antibodies, CDR-grafted antibodies and the like) or other binding proteins which are specific for AFM or AFM variants. Antibodies can be developed using isolated natural or recombinant AFM or AFM variants.

The antibodies are useful in complexes for immunization as well as for purifying polypeptides of the invention. The antibodies are also useful in modulating (i.e., blocking, inhibiting or stimulating) ligand/receptor binding reactions involving AFM.

Anti-idiotypic antibodies specific for anti-AFM antibodies and uses of such anti-idiotypic antibodies in treatment are also contemplated. Assays for the detection and quantification of AFM on cell surfaces and in fluids such as serum may involve a single antibody or multiple antibodies in a "sandwich" assay format.

The uses of the DNA and amino acid sequences of the present invention are varied. For example, knowledge of the sequence of a cDNA for AFM makes possible the isolation by DNA/DNA hybridization of genomic DNA sequences encoding AFM and specifying AFM expression control regulatory sequences such as promoters, operators and the like. DNA/DNA hybridization procedures carried out with DNA sequences of the invention and under stringent conditions are likewise expected to allow the isolation of DNAs encoding allelic variants of AFM, other structurally related proteins sharing the biological and/or immunological specificity of AFM, and proteins homologous to AFM from non-human species (especially from other mammals). DNAs of the invention are useful in DNA/RNA hybridization assays to detect the capacity of cells to synthesize AFM. A variety of specific uses for AFM are disclosed herein below. These uses are primarily based on the known uses of the homologous albumin type polypeptides discussed above.

Also made available by the invention are anti-sense polynucleotides (e.g., DNA and RNA) relevant to regulating expression of AFM by those cells which ordinarily express it. Furthermore, knowledge of the DNA and amino acid sequences of AFM make possible the generation by recombinant means of hybrid fusion proteins characterized by the presence of AFM protein sequences and immunoglobulin heavy chain constant regions and/or hinge regions. See, Capon, et al., Nature, 337: 525–531 (1989); Ashkenazi, et al., P.N.A.S. (USA), 88:10535–10539 (1991); and PCT WO 89/02922, published Apr. 6, 1989.

BRIEF DESCRIPTION OF THE FIGURES

Numerous other aspects and advantages of the present invention will therefore be apparent upon consideration of the following detailed description thereof, reference being made to the drawings wherein:

FIG. 1 shows the nucleotide and deduced amino acid sequence of AFM. The putative signal sequence is indicated in lower case letters. Asterisks indicate putative sites for N-glycosylation. These are also represented as SEQ ID NO:1 AND SEQ ID NO:2.

FIG. 2A and 2B show a comparison of ALB family amino acid sequences. FIG. 2A shows the alignment of ALB family proteins. Sequences were aligned using the Clustal method in the MegAlign program (DNASTAR). Identical amino acid residues are boxed. Consensus indicates residues identical in all 4 sequences. Majority indicates 2 or 3 residues identical in all 4 sequences. FIG. 2B shows percent similarity (right of diagonal) and identity (left of diagonal) between ALB family members. Similarities were determined using the GCG GAP program. The sequences for the comparison proteins are also provided as follows: serum albumin, SEQ ID NO:3; alpha fetoprotein, SEQ ID NO:4; and vitamin D binding protein, SEQ ID NO:5.

DETAILED DESCRIPTION OF THE PREFERRED EMBODIMENTS

Definition of AFM

Figure 3:
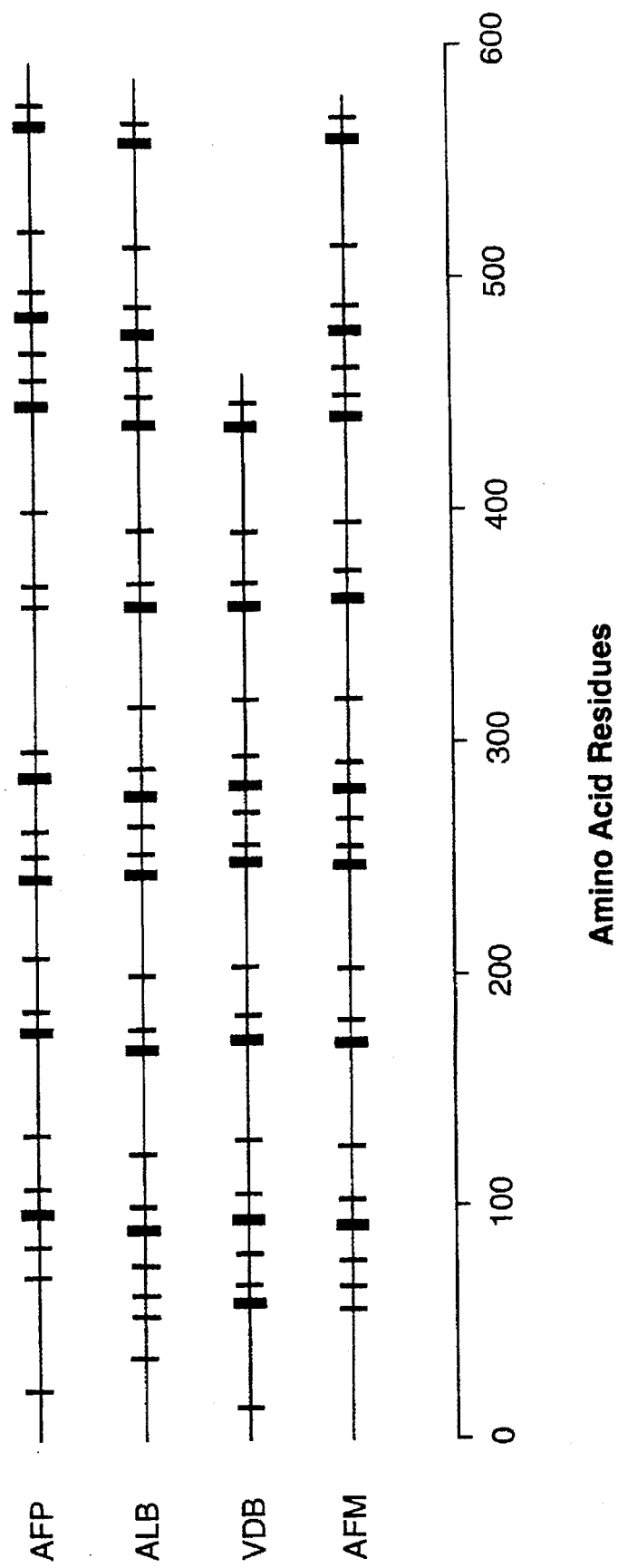
FIG. 3 shows the conserved Cys pattern in ALB family proteins. The mature form of ALB family proteins are depicted with thin vertical bars representing single Cys residues and thick vertical lines representing -Cys-Cys- sequences.

AFM is defined as a polypeptide having a qualitative biological activity or property in common with AFM of FIG. 1.

Included within the scope of AFM as that term is used herein is the AFM having the amino acid sequence of AFM as set forth in FIG. 1, SEQ ID NO:2; glycosylated, deglycosylated or unglycosylated derivatives of AFM; and lipidated or delipidated forms of AFM.

Also included within the scope of AFM are AFMs from any species, including without limitation: human, mouse, rat, pig, rabbit, monkey, dog, etc. Especially preferred is the human form of AFM.

Variants of AFM

Variants of AFM include homologous amino acid sequence variants of the sequence of FIG. 1, and homologous in-vitro-generated variants and derivatives of AFM, which are capable of exhibiting a biological activity or property in common with AFM of FIG. 1.

"Homologous" is used herein to refer to the residues in a candidate sequence that are identical with the residues in the sequence of AFM in FIG. 1 after aligning the sequences and introducing gaps, if necessary, to achieve the maximum percent homology.

A biological activity or property of AFM is defined as either 1) immunological cross-reactivity with at least one epitope of AFM, or 2) the possession of at least one regulatory or effector function qualitatively in common with AFM. Examples of those activities may be found in the section herein describing uses of AFM.

"Immunologically cross-reactive" as used herein means that the candidate polypeptide is capable of competitively inhibiting the qualitative biological activity of AFM or an AFM variant having this activity with polyclonal antisera raised against the known active analog. Such antisera are prepared in conventional fashion by injecting animals such as goats or rabbits, for example, subcutaneously with the known active analog in complete Freund's adjuvant, followed by booster intraperitoneal or subcutaneous injection in incomplete Freund's adjuvant. An example of production of polyclonal antisera production is presented in the examples section below.

Amino acid sequence variants of AFM are prepared with various objectives in mind, including increasing the affinity of AFM for its binding partner, facilitating the stability, purification and preparation of AFM, and the like.

Amino acid sequence variants of AFM fall into one or more of three classes: insertional, substitutional, or deletional variants. These variants ordinarily are prepared by site specific mutagenesis of nucleotides in the DNA encoding AFM, by which DNA encoding the variant is obtained, and thereafter expressing the DNA in recombinant cell culture. However, variant AFM fragments having up to about 100–150 amino acid residues are prepared conveniently by in vitro synthesis.

The amino acid sequence variants of AFM are predetermined variants not found in nature or naturally occurring alleles. AFM variants typically exhibit the same qualitative biological activity as the naturally occurring AFM molecule. However, AFM variants and derivatives that are not capable of binding to their ligands are useful nonetheless (a) as a reagent in diagnostic assays for AFM or antibodies to AFM, (b) when insolubilized in accordance with known methods, as agents for purifying anti-AFM antibodies from antisera or hybridoma culture supernatants, and (c) as immunogens for raising antibodies to AFM or as immunoassay kit components (labeled, as a competitive reagent for the native AFM or unlabeled as a standard for AFM assay) so long as at least one AFM epitope remains active.

While the site for introducing an amino acid sequence variation is predetermined, the mutation per se need not be predetermined. For example, in order to optimize the performance of a mutation at a given site, random or saturation mutagenesis (where all 20 possible residues are inserted) is conducted at the target codon and the expressed AFM variant is screened for the optimal combination of desired activities. Such screening is within the ordinary skill in the art.

Amino acid insertions usually will generally be on the order of about from 1 to 10 amino acid residues; substitutions are typically introduced for single residues; and deletions will generally range about from 1 to 30 residues. Deletions or insertions preferably are made in adjacent pairs, i.e. a deletion of 2 residues or insertion of 2 residues. It will be amply apparent from the following discussion that substitutions, deletions, insertions or any combination thereof are introduced or combined to arrive at a final construct.

Insertional amino acid sequence variants of AFM are those in which one or more amino acid residues extraneous to AFM are introduced into a predetermined site in the target AFM and which displace the preexisting residues. Commonly, insertional variants are fusions of heterologous proteins or polypeptides to the amino or carboxyl terminus of AFM. Such variants are referred to as fusions of AFM and a polypeptide containing a sequence which is other than that which is normally found in AFM at the inserted position. Several groups of fusions are contemplated herein.

Immunologically active AFM derivatives and fusions comprise AFM and a polypeptide containing a non-AFM epitope, and are within the scope of this invention. The non-AFM epitope is any immunologically competent polypeptide, i.e., any polypeptide which is capable of eliciting an immune response in the animal to which the fusion is to be administered or which is capable of being bound by an antibody raised against the non-AFM polypeptide. Typical non-AFM epitopes will be those which are borne by allergens, autoimmune epitopes, or other potent immunogens or antigens recognized by pre-existing antibodies in the fusion recipient, including bacterial polypeptides such as trpLE, beta-galactosidase, viral polypeptides such as herpes gD protein, and the like.

Immunogenic fusions are produced by cross-linking in vitro or by recombinant cell culture transformed with DNA encoding an immunogenic polypeptide. It is preferable that the immunogenic fusion be one in which the immunogenic sequence is joined to or inserted into AFM or fragment thereof by a peptide bond(s). These products therefore consist of a linear polypeptide chain containing AFM epitope and at least one epitope foreign to AFM. It will be understood that it is within the scope of this invention to introduce the epitopes anywhere within the AFM molecule or fragment thereof.

Such fusions are conveniently made in recombinant host cells or by the use of bifunctional cross-linking agents. The use of a cross-linking agent to fuse AFM to the immunogenic polypeptide is not as desirable as a linear fusion because the cross-linked products are not as easily synthesized in structurally homogeneous form.

These immunogenic insertions are particularly useful when formulated into a pharmacologically acceptable carrier and administered to a subject in order to raise antibodies against AFM, which antibodies in turn are useful in diagnostics or in purification of AFM by immunoaffinity techniques known per se. In diagnostic applications, the antibodies will typically be bound to or associated with a detectable group, examples of which are well known to those skilled in the art. Immunoaffinity techniques could be used, for example, to purify AFM.

Other fusions, which may or may not also be immunologically active, include fusions of the mature AFM sequence with a signal sequence heterologous to AFM, and fusions of AFM to polypeptides having enhanced plasma half life (ordinarily>about 20 hours) such as immunoglobulin chains or fragments thereof.

Signal sequence fusions are employed in order to more expeditiously direct the secretion of AFM. The heterologous signal replaces the native AFM signal, and when the resulting fusion is recognized, i.e. processed and cleaved by the host cell, AFM is secreted. Signals are selected based on the intended host cell, and may include bacterial yeast, mammalian and viral sequences. The native AFM signal or the herpes gD glycoprotein signal is suitable for use in mammalian expression systems.

Figure 2A-1:
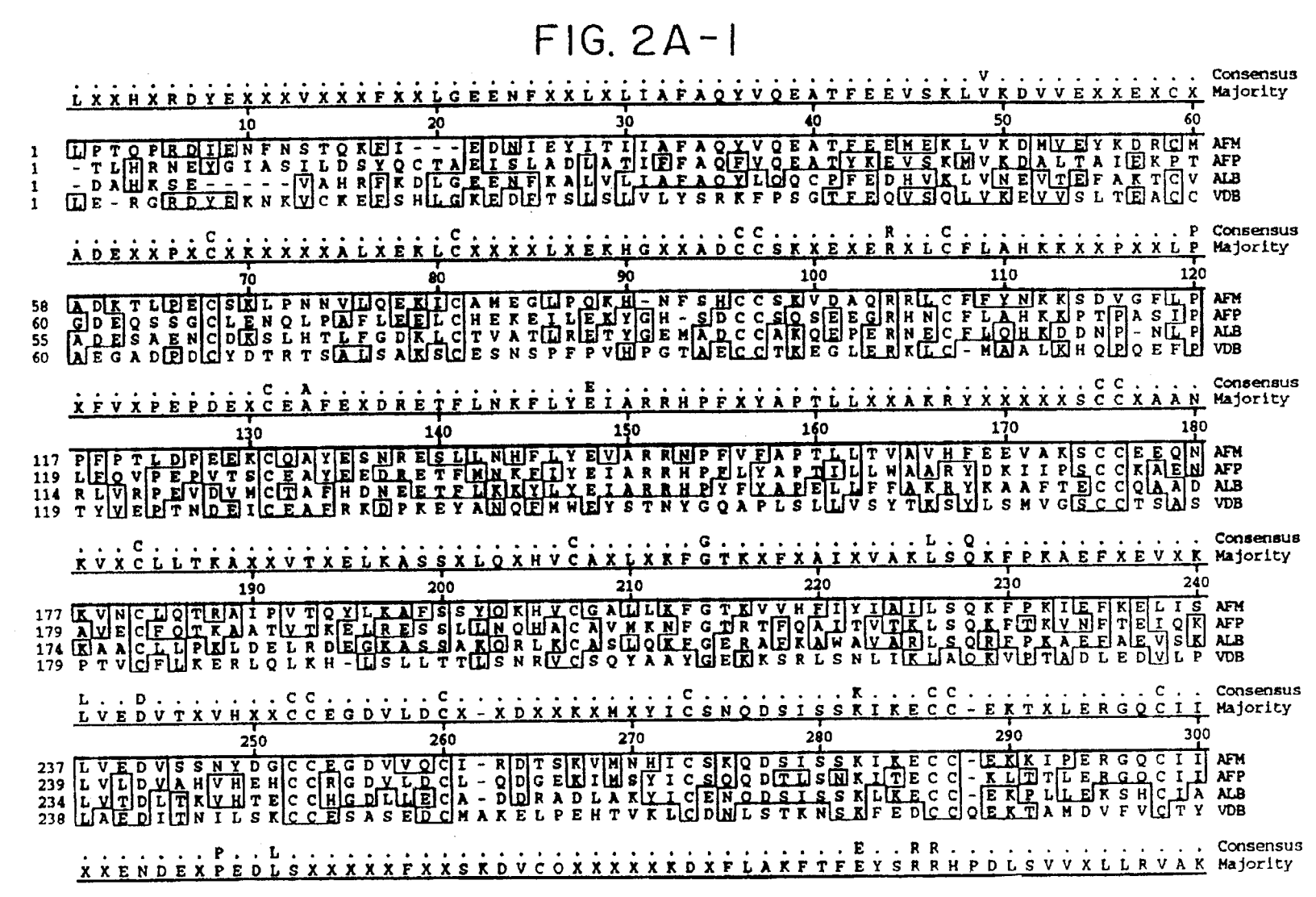
Figure 2A-2:
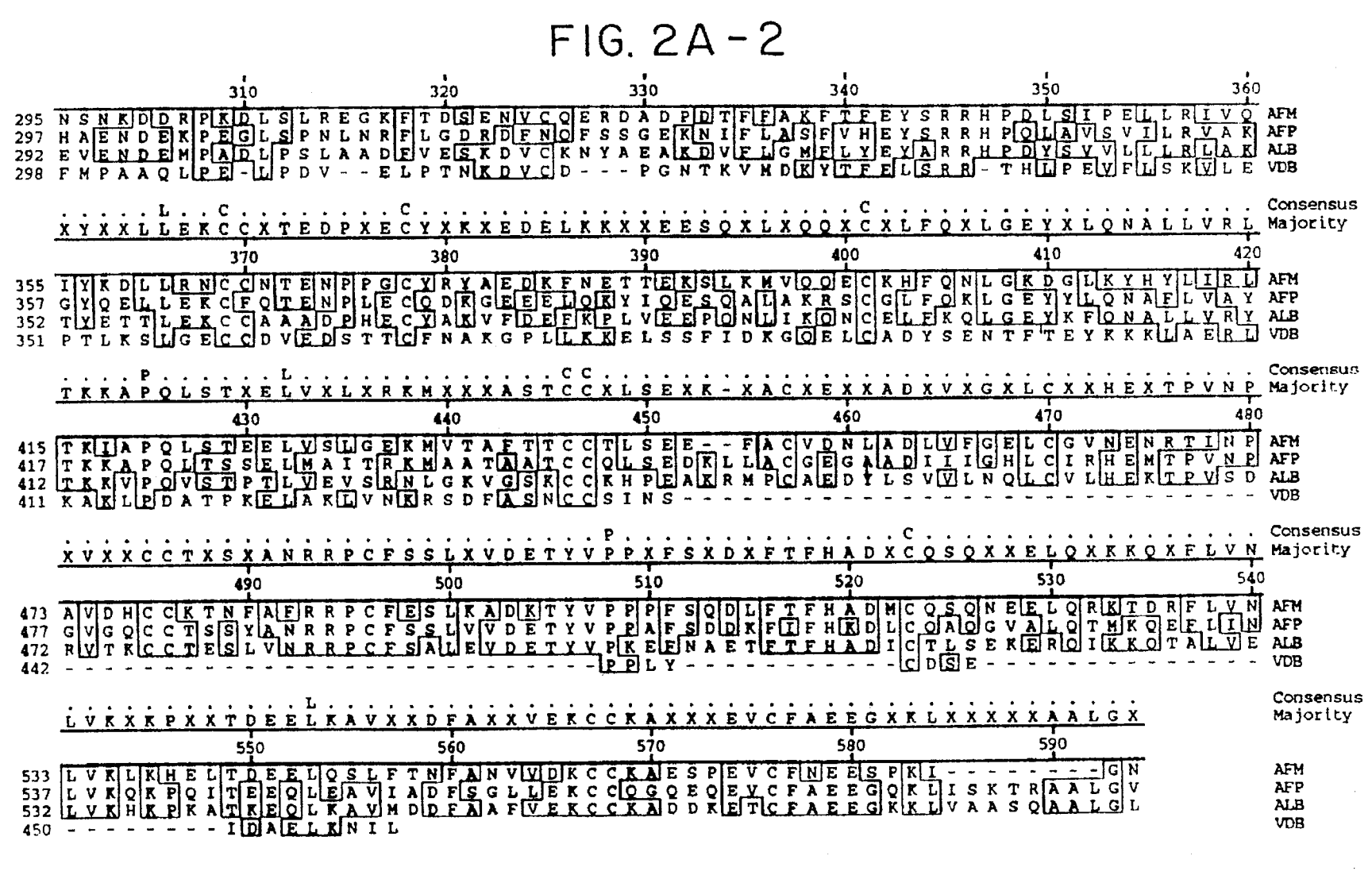

Substantial variants are those in which at least one residue in the FIG. 2 sequence has been removed and a different residue inserted in its place. Such substitutions generally are made in accordance with the following Table 1 when it is desired to finely modulate the characteristics of AFM.

TABLE 1

| Original Residue | Exemplary Substitutions |
| --- | --- |
| Ala | Ser |
| Arg | Lys |
| Asn | Gln; His |
| Asp | Glu |
| Cys | Ser; Ala |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in AFM properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g. glycine.

Some deletions, insertions, and substitutions will not produce radical changes in the characteristics of AFM molecule. However, when it is difficult to predict the exact effect of the substitution, deletion, or insertion in advance of doing so, for example when modifying the AFM extracellular domain or an immune epitope, one skilled in the art will appreciate that the effect will be evaluated by routine screening assays.

Another class of AFM variants are deletional variants. Deletions are characterized by the removal of one or more amino acid residues from AFM sequence. Deletions from the AFM C-terminal or the N-terminal, which preserve the biological activity or immune cross-reactivity of AFM are suitable.

Deletions of cysteine or other labile residues also may be desirable, for example in increasing the oxidative stability of AFM. Deletion or substitutions of potential proteolysis sites, e.g. Arg-Arg, is accomplished by deleting one of the basic residues or substituting one by glutaminyl or histidyl residues.

Preferably, the variants represent conservative substitutions. It will be understood that some variants may exhibit reduced or absent biological activity. These variants nonetheless are useful as standards in immunoassays for AFM so long as they retain at least one immune epitope of AFM.

Glycosylation variants are included within the scope of AFM. They include variants completely lacking in glycosylation (nonglycosylated) and variants having at least one less glycosylated site than the native form (deglycosylated) as well as variants in which the glycosylation has been changed. Additionally, unglycosylated AFM which has the amino acid sequence of the native AFM is produced in recombinant prokaryotic cell culture because prokaryotes are incapable of introducing glycosylation into polypeptides.

Glycosylation variants are produced by selecting appropriate host cells or by in vitro methods. Yeast, for example, introduce glycosylation which varies significantly from that of mammalian systems. Similarly, mammalian cells having a different species (e.g. hamster, murine, insect, porcine, bovine or ovine) or tissue origin (e.g. lung, lymphoid, mesenchymal or epidermal) than the source of AFM are routinely screened for the ability to introduce variant glycosylation as characterized for example by elevated levels of mannose or variant ratios of mannose, fucose, sialic acid, and other sugars typically found in mammalian glycoproteins. In vitro processing of AFM typically is accomplished by enzymatic hydrolysis, e.g. neuraminidase digestion.

AFM isolated from natural sources or produced recombinantly will generally contain bound lipids. The nature of the bound lipids is expected to depend on the source of the AFM. Delipidated versions of AFM may be prepared by standard delipidation methods known in the art, especially the art relating to ALB where delipidation is a common procedure. One preferred method involves extracting an aqueous solution of AFM with a solvent capable of dissolving lipids, such as 1-butanol or diisopropyl ether. Example 8 presents a specific exemplary method for delipidation.

Certain post-translational derivatizations are the result of the action of recombinant host cells on 5 the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl or threonyl residues, methylation of the a-amino groups of lysine, arginine, and histidine side chains (T. E. Creighton, *Proteins: Structure and Molecular Properties,* (W. H. Freeman & Co.), San Francisco: 79–86 (1983), acetylation of the N-terminal amine and, in some instances, amidation of the C-terminal carboxyl.

Oligonucleotides relating to AFM

DNA encoding AFM is synthesized by in vitro methods or is obtained readily from human liver cDNA libraries. The means for synthetic creation of the DNA encoding AFM, either by hand or with an automated apparatus, are generally known to one of ordinary skill in the art, particularly in light of the teachings contained herein. As examples of the state of the art relating to polynucleotide synthesis, one is directed to Maniatis et al., *Molecular Cloning—A Laboratory Manual*, Cold Spring Harbor Laboratory (1984), and Horvath et al., An Automated DNA Synthesizer Employing Deoxynucleoside 3'-Phosphoramidites, *Methods in Enzymology* 154: 313–326 (1987).

Alternatively, to obtain DNA encoding AFM from sources other than murine or human, since the entire DNA sequence for the preferred embodiment of AFM is given, one needs only to conduct hybridization screening with labelled DNA encoding AFM or fragments thereof (usually, greater than about 20, and ordinarily about 50 bp) in order to detect clones which contain homologous sequences in the cDNA libraries derived from the liver of the particular animal, followed by analyzing the clones by restriction enzyme analysis and nucleic acid sequencing to identify full-length clones. If full length clones are not present in the library, then appropriate fragments are recovered from the various clones and ligated at restriction sites common to the fragments to assemble a full-length clone. DNA encoding AFM from other animal species is obtained by probing libraries from such species with the human sequences, or by synthesizing the genes in vitro.

Included within the scope hereof are nucleic acid sequences that hybridize under stringent conditions to a fragment of the DNA sequence in FIG. 1, which fragment is greater than about 10 bp, preferably 20–50 bp, and even greater than 100 bp. Also included within the scope hereof are nucleic acid sequences that hybridize under stringent conditions to a fragment of AFM. "Stringent" is used to refer to conditions that are commonly understood in the art as stringent. An exemplary set of conditions include a temperature of 60°–70° C., (preferably about 65° C.) and a salt concentration of 0.70M to 0.80M (preferably about 0.75M).

Included also within the scope hereof are nucleic acid probes which are capable of hybridizing under stringent conditions to the cDNA of AFM or to the genomic gene for AFM (including introns and 5' or 3' flanking regions extending to the adjacent genes or about 5,000 bp, whichever is greater).

Recombinant Expression of AFM

In general, prokaryotes are used for cloning of DNA sequences in constructing the vectors useful in the invention. For example, E. coli K12 strain 294 (ATCC No. 31446) is particularly useful. Other microbial strains which may be used include E. coli B and E coli X1776 (ATCC No. 31537). Alternatively, in vitro methods of cloning, e.g. polymerase chain reaction, are suitable.

AFMs of this invention are expressed directly in recombinant cell culture as an N-terminal methionyl analog, or as a fusion with a polypeptide heterologous to AFM, preferably a signal sequence or other polypeptide having a specific cleavage site at the N-terminus of AFM. For host prokaryotes that do not process AFM signal, the signal is substituted by a prokaryotic signal selected for example from the group of the alkaline phosphatase, penicillinase, or heat stable enterotoxin II leaders. For yeast secretion the human AFM signal may be substituted by the yeast invertase, alpha factor or acid phosphatase leaders. In mammalian cell expression the native signal is satisfactory for mammalian AFM, although other mammalian secretory protein signals are suitable, as are viral secretory leaders, for example the herpes simplex gD signal.

AFM may be expressed in any host cell, but preferably are synthesized in mammalian hosts. However, host cells from prokaryotes, fungi, yeast, insects and the like are also are used for expression. Exemplary prokaryotes are the strains suitable for cloning as well as E. coli W3110 (F-, 1-, prototrophic, ATTC No. 7325), other enterobacteriaceae such as Serratia marescans, bacilli and various pseudomonads. Preferably the host cell should secrete minimal amounts of proteolytic enzymes.

Expression hosts typically are transformed with DNA encoding AFM which has been ligated into an expression vector. Such vectors ordinarily carry a replication site (although this is not necessary where chromosomal integration will occur). Expression vectors also include marker sequences which are capable of providing phenotypic selection in transformed cells, as will be discussed further below.

Expression vectors also optimally will contain sequences which are useful for the control of transcription and translation, e.g., promoters and Shine-Dalgarno sequences (for prokaryotes) or promoters and enhancers (for mammalian cells). The promoters may be, but need not be, inducible.

Promoters suitable for use with prokaryotic hosts illustratively include the β-lactamase and lactose promoter systems (Chang et al., Nature, 275, 615 (1978); and Goeddel et al., Nature 281, 544 (1979)), alkaline phosphatase, the tryptophan (trp) promoter system (Goeddel, Nucleic Acids Res. 8:4057 (1980) and EPO Appln. Publ. No. 36,776) and hybrid promoters such as the tac promoter (H. de Boer et al., Proc. Natl. Acad. Sci. USA 80, 21–25 (1983)). However, other functional bacterial promoters are suitable. Their nucleotide sequences are generally known, thereby enabling a skilled worker operably to ligate them to DNA encoding AFM (Siebenlist et al., Cell 20, 269 (1980)) using linkers or adapters to supply any required restriction sites. Promoters for use in bacterial systems also will contain a Shine-Dalgarno (S.D.) sequence operably linked to the DNA encoding AFM.

In addition to prokaryotes, eukaryotic microbes such as yeast or filamentous fungi are satisfactory. Saccharomyces cerevisiae is the most commonly used eukaryotic microorganism, although a number of other strains are commonly available.

Suitable promoting sequences for use with yeast hosts include the promoters for 3-phosphoglycerate kinase (Hitzeman et al., J. Biol. Chem. 255, 2073 (1980)) or other glycolytic enzymes (Hess et al., J. Adv. Enzyme Reg. 7:149 (1968); and Holland, Biochemistry 17, 4900 (1978)), such as enolase, glyceraldehyde-3-phosphate dehydrogenase, hexokinase, pyruvate decarboxylase phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde 3-phosphate dehydrogenase, and enzymes responsible for maltose and galactose utilization. Suitable vectors and promoters for use in yeast expression are further described in R. Hitzeman et al., European Patent Publication No. 73,657A.

Expression control sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence which may be the signal for addition of the poly A tail to the 3' end of the coding sequence. All of these sequences are inserted into mammalian expression vectors.

Suitable promoters for controlling transcription from vectors in mammalian host cells are readily obtained from various sources, for example, the genomes of viruses such as polyoma virus, SV40, adenovirus, MMV (steroid inducible), retroviruses (e.g. the LTR of HIV), hepatitis-B virus and most preferably cytomegalovirus, or from heterologous mammalian promoters, e.g. the beta actin promoter. The early and late promoters of SV40 are conveniently obtained as an SV40 restriction fragment which also contains the SV40 vital origin of replication. Fiers et al., Nature 273, 113

(1978). The immediate early promoter of the human cytomegalovirus is conveniently obtained as a HindIII E restriction fragment. Greenaway, P. J. et al., *Gene* 18, 355–360 (1982).

Transcription of a DNA encoding AFM by higher eukaryotes is increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins, L. et al., *PNAS* 78, 993 (1981)) and 3' (Lusky, M. L., et al., *Mol. Cell Bio.* 3, 1108 (1983) to the transcription unit, within an intron (Banerji, J. L. et al., *Cell* 33:729 (1983)) as well as within the coding sequence itself (Osborne, T. F., et al., *Mol. Cell Bio.* 4, 1293 (1984)). Many enhancer sequences are now known from mammalian genes (globin, elastase, albumin, a-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding AFM. The 3' untranslated regions also include transcription termination sites.

Expression vectors may contain a selection gene, also termed a selectable marker. Examples of suitable selectable markers for mammalian cells are dihydrofolate reductase (DHFR), thymidine kinase (TK) or neomycin.

Suitable eukaryotic host cells for expressing AFM include monkey kidney CV1 line transformed by SV40 (COS-7, ATCC CRL 1651); human embryonic kidney line (293 or 293 cells subcloned for growth in suspension culture, Graham, F. L. et al., *J. Gen Virol.* 36:59 (1977)); baby hamster kidney cells (BHK, ATCC CCL 10); Chinese hamster ovary-cells-DHFR (CHO, Urlaub and Chasin, *PNAS (USA)* 77, 4216, (1980)); mouse sertoli cells (TM4, Mather, J. P., *Biol. Reprod.* 23, 243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather, J. P. et al., *Annals N.Y. Acad. Sci.* 383, 44–68 (1982)).

Construction of suitable vectors containing the desired coding and control sequences employ standard ligation techniques. Isolated plasmids or DNA fragments are cleaved, tailored, and religated in the form desired to form the plasmids required.

Host cells are transformed with the expression vectors of this invention and cultured in conventional nutrient media modified as appropriate for inducing promoters, selecting transformants or amplifying AFM gene. The culture conditions, such as temperature, pH and the like, are those previously used with the host cell selected for expression, and will be apparent to the ordinarily skilled artisan.

The host cells referred to in this disclosure encompass cells in in vitro culture as well as cells which are within a host animal.

"Transformation" means introducing DNA into an organism so that the DNA is replicable, either as an extrachromosomal element or by chromosomal integration. The method used herein for transformation of the host cells may be, for example, the method of Graham, F. and van der Eb, A., *Virology* 52, 456–457 (1973). However, other methods for introducing DNA into cells such as by nuclear injection or by protoplast fusion may also be used. If prokaryotic cells or cells which contain substantial cell wall constructions are used, the preferred method of transfection is calcium treatment using calcium chloride as described by Cohen, F. N. et al., *Proc. Natl. Acad. Sci. (USA)* 69, 2110 (1972).

"Transfection" refers to the introduction of DNA into a host cell whether or not any coding sequences are ultimately expressed. Numerous methods of transfection are known to the ordinarily skilled artisan, for example, $CaPO_4$ and electroporation. Transformation of the host cell is indicative of successful transfection.

Recovery and Purification of AFM

AFM is recovered and purified from recombinant cell cultures by known methods, including ammonium sulfate or ethanol precipitation, acid extraction, anion or cation exchange chromatography, phosphocellulose chromatography, immunoaffinity chromatography, hydroxyapatite chromatography, lectin chromatography, hydrophobic interaction chromatography, and gel filtration chromatography. Other known purification methods within the scope of this invention utilize, for example, immobilized carbohydrates, epidermal growth factor, or complement domains. Moreover, reverse-phase HPLC and chromatography using anti-AFM antibodies are useful for the purification of AFM. AFM may preferably be purified in the presence of a protease inhibitor such as PMSF. A specific preferred method of purifying AFM is found in Example 1.

Uses of AFM

As mentioned above, in view of the homology between AFM and each of ALB, AFP and VDB, it is expected that AFM and variants thereof will have identical or similar biological activities and utilities. In general, members of the albumin family show a high propensity to bind and transport a wide variety of substances through the body including fatty acids, hormones, enzymes, dyes, trace metals and drugs. It is expected that a preparation of AFM which has its endogenous lipids removed could be used to reduce high concentrations of free fatty acids (hyperlipidemia) found in disease states such as acute pancreatitis, ARDS, sepsis and atherosclerosis.

Similar to proposed functions for ALB, AFM can also potentially be used as an antioxidant. AFM is expected to act as an antioxidant by sequestering metal ions and preventing those ions from accelerating free-radical reactions (ie. decomposition of lipid peroxides to peroxy and alkoxy radicals; formation of hydroxyl radical from hydrogen peroxide) or AFM may act to directly inactivate hydrogen peroxide, hydroxyl radicals and hypochlorous acid. The detoxification of oxygen metabolites by AFM can limit the detrimental effects that unbound oxygen metabolites have in inactivating beneficial anti-proteases ($a_1$-antiproteinase and $a_1$-antitrypsin) and in damaging DNA, proteins and lipids. Thus, AFM may be used to ameliorate ischaemia-reperfusion injury, rheumatoid arthritis, ARDS, cardiopulmunary bypass, sepsis and any other diseases or tissue damage caused by an excess production of oxygen metabolites from leukocytes and/or arachidonic acid metabolism.

Another use of AFM is based on the finding that albumin family proteins bind and detoxify a wide variety of toxic products including man-made drugs. Thus, AFM can ameliorate the effects of toxic plasma substances released as a result of inflammation and can be conjugated to toxic pharmaceuticals so as to minimize detrimental activities of the drug.

AFM may also have anticoagulant properties as has been reported for ALB. AFM may inhibit platelet aggregation and thus could be a useful additive to resuscitation fluids in disease states characterized by increased platelet aggregation such as sepsis, hemmorrhagic shock and burn injury.

Serum AFM levels may increase or decrease due to a particular pathological condition as has been observed with AFP. Thus, calculation of serum AFM levels using antibodies described in Example 11 will be useful in diagnosing specific human diseases.

Administration of AFM

For administration in vivo, AFM is placed into sterile, isotonic formulations, and administered by standard means well known in the field. The formulation of AFM is preferably liquid, and is ordinarily a physiologic salt solution containing 0.5–10 mM calcium, non-phosphate buffer at pH 6.8–7.6, or may be lyophilized powder.

It is envisioned that intravenous delivery, or delivery through catheter or other surgical tubing will be the primary route for therapeutic administration. Alternative routes include tablets and the like, commercially available nebulizers for liquid formulations, and inhalation of lyophilized or aerosolized receptors. Liquid formulations may be utilized after reconstitution from powder formulations.

AFM may also be administered via microspheres, liposomes, other microparticulate delivery systems or sustained release formulations placed in certain tissues including blood.

The dose of AFM administered will be dependent upon the properties of AFM employed, e.g. its activity and biological half-life, the concentration of AFM in the formulation, the administration route for AFM, the site and rate of dosage, the clinical tolerance of the patient involved, the pathological condition afflicting the patient and the like, as is well within the skill of the physician.

AFM may also be administered along with other pharmacologic agents such as antibiotics, anti-inflammatory agents, and anti-tumor agents. It may also be useful to administer AFM along with other therapeutic proteins such as gamma-interferon and other immunomodulators.

Ligands of AFM

It is also posible that the AFM of the present invention will have an additional natural ligand or ligands (other than the lipids discussed herein) and that such ligands will be capable of modulating the biological activities of AFM in vivo. One of ordinary skill may be able to utilize the teachings of the present invention to screen for ligands of the AFMs disclosed herein and then isolate and purify them, e.g., by immunochromatography using AFM or a variant of AFM bound to a solid support.

Antibodies to AFM

Also included within the scope of the invention are antibodies (e.g., monoclonal and polyclonal antibodies, single chain antibodies, chimeric antibodies, CDR-grafted antibodies and the like) or other binding proteins which are specific for AFM or its variants. Antibodies can be developed using natural or recombinant AFM or AFM variants or cells expressing such molecules on their surfaces. Active fragments of such antibodies are also contemplated.

The antibodies are useful for purifying the polypeptides described herein, or identifying and purifying cells producing the polypeptides on their surfaces. The antibodies could also be used to modulate (e.g., block, inhibit or stimulate) ligand binding to AFM. Anti-idiotypic antibodies are also contemplated. Assays for detection and quantitation of AFM on cell surfaces and in fluids (such as serum, blood, cerebrospinal fluid, urine, semen, milk, and tears) may involve a single antibody or a "sandwich" assay format.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below. All literature and patent citations herein are expressly incorporated by reference.

EXAMPLES

Example 1

Lipopolysaccharide (LPS) Neutralization Assay

A. Formation of ELPS.

Sheep erythrocytes are first coated with *S. minnesota* Re595 LPS (List Biological) as previously described (*J. Ex. Med.* 170:1231). The concentration of LPS used to coat erythrocytes is 10 mg/8×10$^7$ erythrocytes. After coating with LPS, erythrocytes are resuspended in 5 mM veronal buffer, pH 7.5, containing 150 mM NaCl, 0.1% gelatin and 1 mM EDTA (EDTAGVB$^{2-}$) to a concentration of 1×10$^8$ cells/ml.

B. Opsonization of ELPS. ELPS are opsonized using normal human plasma (NHP) as a source of opsonizing proteins (septin) (*J. Ex. Med.* 176:719) or LBP (*J. Ex. Med.* 170:1231). NHP is diluted 1:100 in phosphate buffered saline without divalent cations containing 1 mM EDTA (PDEDTA) and then mixed 1:1 with ELPS (1×10$^8$ cells/ml). The mixture is then incubated 10 minutes at 37° C. spun down for 1 minute at 800x g in a swinging bucket centrifuge. Cells are washed 2× with EDTAGVE$^{2-}$ and resuspended to a final concentration of 1×10$^8$ cells/ml in EDTAGVB$^{2-}$. Erythrocytes treated as above are denoted E-septins.

C. Assay of Samples for LPS Neutralizing Activity. The following step measures the ability of a given sample to reduce the amount of binding of LPS coated erythrocytes to macrophages in a CD-14 dependent manner. Dilutions of samples to be tested are made in PDEDTA. E-septins are incubated 1:1 with sample dilutions at 37° C. for 40 minutes. One sample is included in which E-septin is incubated with PDEDTA alone as a control. Following incubation, E-septins are spun down in a swinging bucket centrifuge at 800x g for 1 minute and resuspended in EDTAGVB$^{2-}$ to a concentration of 1×10$^8$ cells/ml. E-septins treated in this manner are denoted E-septin$^1$. Five ml of the resuspended E-septins$^1$ are added to a macrophage monolayer (see below) in a 60 well terasaki plate (NUNC, Inc.). The plate is incubated 20 minutes at room temperature followed by inversion and incubation another 12 minutes at room temperature to separate unbound E-septins$^1$ from the macrophages. The plate is then dipped in a beaker of cold PBS with no divalent cations containing 0.001% azide to wash off unbound erythrocytes. Binding of E-septins$^1$ is evaluated by phase contrast microscopy. Binding is expressed as the attachment index which denotes the number of erythrocytes bound per 100 macrophages. LPS neutralizing activity of the samples is evaluated by comparing the binding of E-septins$^1$ incubated with dilutions of the sample in PDEDTA to E-septin$^1$ incubated with PDEDTA alone. Activity is measured in units/ml. This represents the dilution at which the sample reduces E-septin$^1$ binding by 50% in the standard assay.

D. Macrophage Monolayer. Monocyte derived macrophages are obtained by culturing human monocytes in teflon beakers as described (*J. Ex. Med.* 156:1149). On the day of the assay, macrophages are removed from the beaker, washed with PBS containing divalent cations (PBS$^{2+}$) and resuspended in PBS$^{2+}$ containing 0.5 mg/ml human serum albumin (Armour Pharm.), 0.3 U/ml aprotinin (Sigma) and 3 mM glucose (HAP buffer) to 1×10⁶ cells/ml. Thirty minutes prior to addition of E-septins[1] to the terasaki plate, macrophage monolayers are formed by adding 5 ml of cells and 5 ml of HAP buffer to each well. Immediately prior to addition of E-septins[1], the plate is flooded with PDEDTA and the wells are lightly aspirated.

Example 2

Purification of AFM

All steps, except where noted were done at controlled room temperature. All buffers were made with pyrogen free water and sterile filtered prior to use. One unit of fresh frozen plasma (FFP) was thawed by immersion of the packet in a room-temperature water bath. The thawed plasma was first transferred to a graduated cylinder, the volume noted, and then poured into a beaker. The FFP was then stirred magnetically while the beaker was immersed in a ice-water bath. To the FFP, sufficient 3.9M ammonium sulfate (4° C.) was slowly added to achieve a final ammonium sulfate concentration of 1.6M. This mixture was allowed to stir at 4° C. for an additional 4 hours. The mixture was then centrifuged at 10,000 x g for 60 minutes. The supernatant was recovered and allowed to come to room temperature by immersion in a room temperature water bath.

A portion (250 ml) of the ammonium sulfate supernatant was loaded onto a 2.6×10 cm Phenyl Sepharose HP column previously equilibrated with 50 mM sodium phosphate, 1.6M ammonium sulfate; pH 7.5. Loading, wash and elution steps were done at a linear flow rate of 40 cm/hr. Following sample loading the column was washed in turn with 50 mM sodium phosphate, 1.6M ammonium sulfate; pH 7.5 and 50 mM sodium phosphate; pH 7.5. Elution of activity (see Example 1) was accomplished by the introduction of water. The pH of the water eluate was adjusted to 8.2 with 0.1M Tris base and loaded, at a flow rate of 150 cm/hr, onto a 2.6×10 cm Q Sepharose HP column previously equilibrated with 20 mM Tris-HCl; pH 8.2. Following sample loading the column was thoroughly washed with first 20 mM Tris-HCl; pH 8.2 and then 0.1M sodium chloride, 20 mM Tris-HCl; pH 8.2. The column was then resolved with a 0.33 mM/ml linear gradient of sodium chloride ranging from 0.1 to 0.3M, followed by a 7 mM/ml linear gradient of sodium chloride ranging from 0.3M to 1.0M in 20 mM Tris-HCl; pH 8.2. Active fractions were pooled (30 ml).

One third of the pooled activity from above was loaded onto a Superdex 200 prep column (2.6×60 cm) previously equilibrated with phosphate buffered saline; pH 7.4. The column was loaded and resolved at a flow rate of 1 ml/min. The fractions were analyzed for activity and by reducing SDS-PAGE. A pool (8ml) of the appropriate fractions showed two major protein bands by reducing SDS PAGE at a molecular weight of 87 kd and 28 kd. Two milliliters of the above pool was submitted for sequence analysis. The 28 kd protein had the same N-terminus as ApoA1 and the 87 kd protein had a novel N-terminus (see below). The remaining 6ml of the Superdex 200 prep pool was loaded onto a Superdex 200 prep column(2.6×60 cm) previously equilibrated with 1% sodium deoxycholate, 0.15M sodium chloride, 50 mM Tris-HCl; pH 8.5. The column was loaded and resolved at a flow rate of 1 ml/min. The fractions were analyzed by SDS-PAGE. Those fractions corresponding to either the 87 kd or the 28 kd proteins were separately pooled (16 ml each).

Four milliliters of each pool was diafiltered against 50 mM Tris-HCl; pH 8.5 to remove excess sodium deoxycholate and concentrated to approximately 0.1 mg/ml.

Example 3

Amino Acid Sequence Analysis of N-terminus and Proteolytic Fragments of Purified AFM To obtain the N-terminal sequence, 10 ug of purified AFM was loaded on the reverse phase portion of a precycled biphasic sequencing column. The column was loaded on a Hewlett Packard G1004A protein sequencer with on-line phenylthiohydantoin amino acid analysis performed with a Hewlett Packard 1090 high performance liquid chromatography (HPLC). The N-terminal amino acid sequence obtained from the protein was:

LPTQPRDIENFXSTQKFIEDNIEYITIIAFAQYV(SEQ ID NO: 6), where "X" represents an unassignable amino acid.

To obtain sequences from AFM tryptic peptide fragments, 100 mg of AFM was dissolved in 8M urea with 0.4M ammonium bicarbonate, then reduced with DTT and carboxymethylated with iodoacetic acid. The sample was subsequently diluted with water to adjust the urea concentration to 2M, then digested with sequencing grade trypsin (Boehringer Mannheim) at 37° C. for 18 h with an enzyme to substrate ratio of 1:50. The digested protein was injected on a Hewlett Packard 1090 HPLC equipped with a 4.6×250 mm C18 reverse phase column (Vydac). Elution was performed using a linear gradient of acetonitrile with 0.1% trifluoroacetic acid at a flow rate of 0.75 ml/min. Elution was monitored at 214 nm and fractions were collected. Selected fractions were run on the Hewlett Packard G1004A protein sequencer as described above. The amino acid sequences obtained from select tryptic fragments are summarized in Table 1.

TABLE 1

| Trypsin fragments | | |
|---|---|---|
| FX18 | YHYLIR | (SEQ ID NO: 7) |
| FX20 | FTFEYSR | (SEQ ID NO: 8) |
| FX27 | FTDSENVCQERDADP | (SEQ ID NO: 9) |
| FX29 | IVQIYKDLLR | (SEQ ID NO: 10) |
| FX32 | IAPQLSTEELVSLGE | (SEQ ID NO: 11) |
| FX37 | RHPDLSIPELLR | (SEQ ID NO: 12) |
| FX45 | ESLLNHFLYEVAR | (SEQ ID NO: 13) |
| FX53 | RNPFVFAPTLLTVAVHFEEVAKSCC | (SEQ ID NO: 14) |

Example 4

Isolation of AFM cDNA

The polymerase chain reaction (PCR) was used to amplify a portion of the AFM gene from which an exact probe could be derived. A PCR (PCR 1) was first performed with fully degenerate primers specifying the sense strand for the N-terminal amino acid sequence QKFIEDN (SEQ ID NO: 15) [5' ACG CTG AAT TCG CCA (GA)AA (GA) TT (CT)AT (ATC)GA (GA) GA (CT)AA] (SEQ ID NO: 16) and the antisense strand for a portion of the FX 29 tryptic peptide sequence IVQIYKD (SEQ ID NO: 17) [5' ACG CTA AGC TTG C(GA) T C(CT)T T(GA) T A(GAT)A T(CT)T G(AGCT)A C(GAT)A T] (SEQ ID NO: 18). One ng of Quick Clone Human liver cDNA (Clontech, cat. no. 7113-1) was used as the template in a 100 ml PCR performed in a standard buffer (Perkin-Elmer Cetus) with 1 mM of each degenerate primer. The cycling parameters used in the PCR were as follows: 95° C., 8 min (1 cycle); 94° C., 1 min, 34° C., 10 min, 72° C., 2 min (3 cycles); 94° C., 1 min, 50° C., 1 min, 72° C., 2 min (45 cycles); 72° C., 5 min (1 cycle).

Agarose gel analysis of PCR 1 did not reveal the amplification of any specific products, thus we utilized an aliquot of PCR 1 as a template for a second PCR (PCR 2) using a nested primer pair. For this experiment, we used fully degenerate primers specifying the sense strand for the N-terminal amino acid sequence DNIEYIT (SEQ ID NO: 19) [5' ACG CTG AAT TCG CGA (CT)AA (CT)AT (ATC) GA (GA)TA (CT)AT (ATC)AC](SEQ ID NO: 20) and the antisense strand for the FX 20 tryptic peptide sequence FTFEYS (SEQ ID NO: 21) [5' ACG CTA AGC TTG C(GATC)G A(GA)T A(CT)T C(GA)A A(ACGT)G T(GA)A A] (SEQ ID NO: 22). PCR 2 was then performed using the same reaction mix and cycling parameters as PCR 1, except for the substitution of 1 ml of PCR 1 in place of the human liver cDNA. Analysis of PCR 2 by agarose gel electrophoresis revealed the amplification of a 1 kb product.

To prepare PCR 2 for DNA sequencing, the inventors utilized the EcoR I and Hind III sites that were incorporated into the degenerate primers. These sites were used to clone the fragment into mp19 (Boehringer Mannheim). The 1 kb PCR 2 product cloned in mp19 (mp19 AFM) was then sequenced in its entirety from both strands. Nucleotide sequence analysis of the fragment confirmed that we had amplified a segment of AFM cDNA as the sequence was found to have an open reading frame which encoded 3 tryptic peptides that were already sequenced (Table 1, Fxs 27, 45, 53). The nucleotide sequence of the 1 kb fragment was compared to all sequences in the Genbank database and found to be unique. We also observed that the partial AFM cDNA had significant homology with cDNAs reported for ALB family proteins (ALB, AFP and VDB). Therefore, in order to to isolate a full-length cDNA encoding AFM and to minimize the probability of hybridizing other ALB family genes, we screened a human liver cDNA library with an exact 18mer oligonucleotide (5' TAT GTG CTA TGG AGG GGC) (SEQ ID NO: 23) derived from a segment of AFM sequence that was not highly homologous to ALB, AFP and VDB. The oligonucleotide was end-labeled with $^{32}P_i$ and used to screen a human liver cDNA library (Clontech, cat. no. HL1115a). Positive clones were purified and rescreened with the same oligonucleotide probe. A single positive clone (17AFM) with a 2.3 kb insert was chosen for further study and phage DNA was prepared. The 2.3 kb insert was then sequenced in its entirety from both strands and verified to encode AFM.

This approach enabled the inventors to isolate a lambda phage (17AFM) containing full-length AFM cDNA.

Example 5

Characterization of AFM

The insert in 17AFM is 2287 bp (FIG. 1) consisting of a 317 bp 5' untranslated region, a 1797 bp sequence encoding a protein of 599 amino acids and a 173 bp 3' untranslated region. The predicted amino acid sequence of AFM was found to contain all the tryptic peptides (See Table 1) that had been previously sequenced from the purified protein. Translation of the AFM cDNA sequence reveals that a 21 amino acid hydrophobic leader peptide precedes the experimentally determined N-terminus of mature AFM. The mature AFM is predicted to have 578 amino acids with a calculated Mr of 66576 and pI of 5.65. The difference between the calculated Mr of AFM and its apparent molecular weight on SDS-PAGE is likely due to glycosylation. AFM has 4 potential sites for N-glycosylation (FIG. 1) and N-glycanase treatment reduced the apparent Mr of AFM to 65000 when analyzed by reducing SDS-PAGE (data not shown).

Figure 4A:
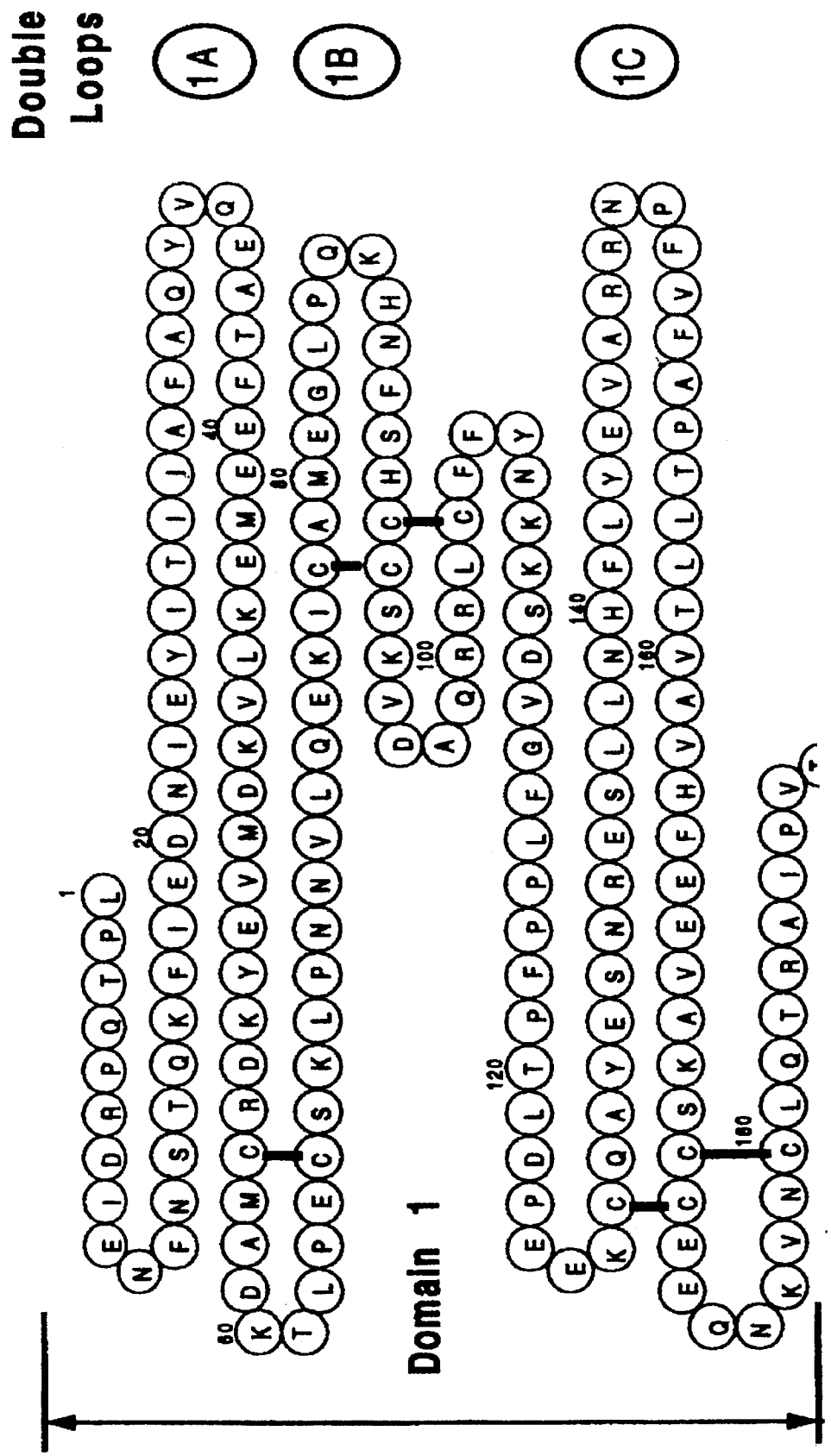
FIG. 4 shows the putative disulfide bonding pattern for AFM. The organization of domains and double loops are drawn as originally proposed for ALB.
Figure 4B:
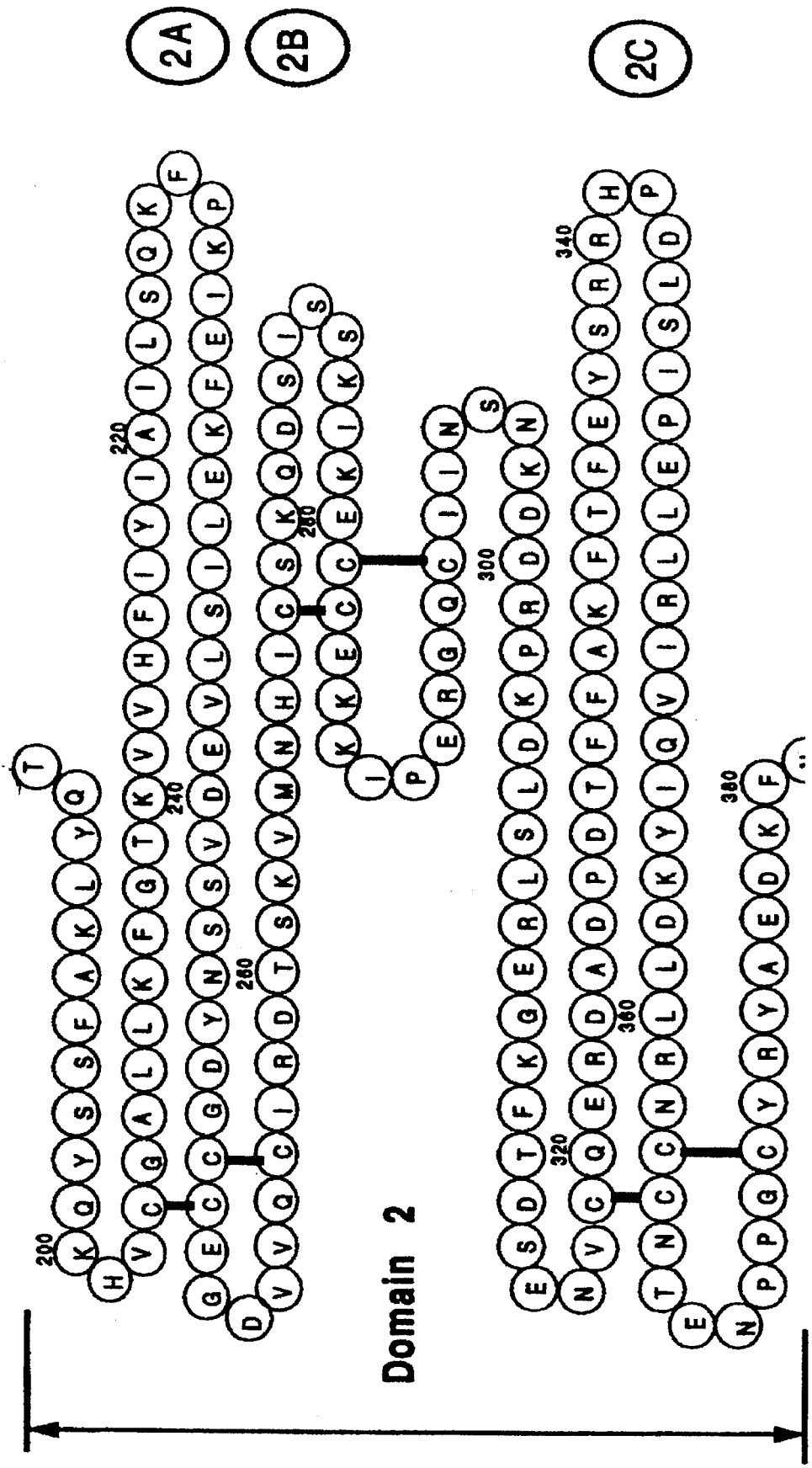

A comparison of the deduced AFM amino acid sequence and other ALB family sequences is shown in FIG. 2. It is evident there is strong similarity between AFM and other ALB family members throughout the entire protein. When conserved amino acids are taken into account, the of AFM to AFP, ALB and VDB is 60.4%, 54.8% and 41.2% respectively. The distribution of Cys residues is conserved among ALB family members. The positions of AFM Cys residues are clearly consistent with this arrangement (FIG. 3). The Cys residues in ALB family proteins have also been proposed to form a pattern of disulfide bridges enabling these proteins to be depicted as a series of 9 double loops defining 3 structural domains. FIG. 4 shows that the 34 Cys residues in AFM can be arranged into a pattern of 17 disulfide-linked pairs that parallels the domain organization observed in other ALB family proteins.

Example 6

Chromosomal Mapping

PCR was performed on a panel of somatic cell hybrids (Bios Laboratories, cat. no. CP2-02) to identify the chromosomal location of the gene. For PCR, we utilized primers (5' CAA CCC TGC TGT GGA CCA C; 5' GCA CAT ATG TTT TAT CAG CTT T) (SEQ ID NO: 24 and SEQ ID NO: 25) that would be expected to amplify an 88 bp fragment between nt 1790 and 1878 in the AFM cDNA. Each PCR on somatic cell hybrid DNA was performed in a standard 100 ml reaction mixture (Perkin-Elmer Cetus) containing 250 ng DNA and a final concentration of 0.1 mM of each primer. The cycling parameters were as follows: 95° C., 5 min (1 cycle); 94° C., 1 min, 56° C., 1 min, 72° C., 1 min (25 cycles); 72° C., 5 min (1 cycle).

Utilizing PCR on a panel of commercially available somatic cell hybrids (data not shown), we detected an amplified product in only 2 hybrids. Both of these hybrids had DNA in common from human chromosomes 4, 5 and 8. Since PCRs performed on hybrids containing DNA from chromosomes 5 and 8 did not yield amplified products, we conclude that AFM resides on human chromosome 4 along with other ALB family genes.

Example 7

Stable Expression of rAFM

Two separate PCR's were performed on AFM cDNA to generate 2 overlapping fragments that span the entire AFM cDNA sequence. The oligonucleotide pair (5' TCA CCT CTA GAC CAC CAT GAA ACT ACT AAA ACT TAC AG+5' AAT TTC TCA GGA GAT CTT TGT ATA) (SEQ ID NO: 26 and SEQ ID NO: 27) used in the first PCR introduced an Xba I site and a perfect Kozak sequence preceeding the AFM initiator codon. The amplified product was subsequently cloned into pGEMT (Promega) to create pDJ11. The oligonucleotide pair (5' AAA TAT ACA AAG ATC TCC TGA GAA 5' TCC CGG TCG ACT CAG TTG CCA ATT TTT GGA C) (SEQ ID NO: 28 and SEQ ID NO: 29) used in the second PCR introduced a Sal I site following the natural stop codon in AFM and the product was cloned into pGEMT to create pDJ13. The 3' end of AFM was then joined to the 5' end by ligating a Bgl II-Sal I fragment from pDJ13 into pDJ11 that had been digested with Bgl II and Sal I. The resultant plasmid (pDJ14) was then digested with Xba I and Sal I and the entire AFM cDNA was cloned into the mammalian expression vector pDSRa (European Patent Application A20398753) that was modified to include unique Xba I and Sal I sites. The AFM expression vector was used to transfect a Chinese Hamster Ovary (CHO) cell line deficient in dihydrofolate reductase (CHO D⁻). Transfectants were selected in medium lacking hypoxanthine and thymidine. An RNase protection assay was used to screen for transfectants that had AFM-specific mRNA. A single clone was grown without serum as described (See, Bourdrel, L. et al., *Protein Expression Purif.* 4:130 (1993) to generate conditioned medium (CM) containing rAFM.

Figure 5:
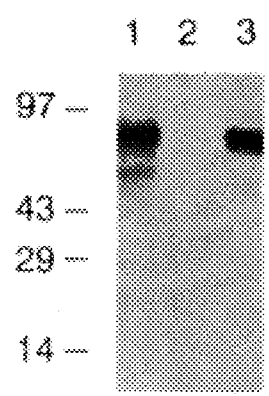
FIG. 5 shows the expression of rAFM in stably transfected CHO D$^-$ cells. Samples were applied to SDS-PAGE under reducing conditions followed by electrophoretic transfer to nitrocelluose. After blocking with skim milk, the membrane was probed with the AM339 antibody followed by incubation with donkey rabbit anti-Ig. Immunoreactive proteins were visualized by chemiluminescence. Lane 1, 80 ml conditioned medium (CM) from CHO D$^-$ cells transfected with AFM cDNA; lane 2, 80 ml CM from nontransfected CHO D$^-$ cells; lane 3, 100 ng AFM purified from human plasma. Size markers (in kDa) are indicated on the left.
Figure 6:
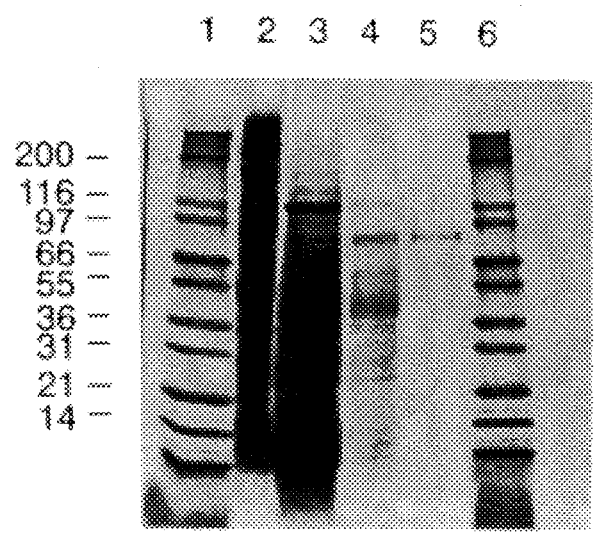
FIG. 6 shows purification of rAFM. Samples purified from CHO D$^-$ cells transfected with AFM cDNA were adjusted with an equal volume of 2× sample buffer (125 mM Tris-HCl, pH 6.8, 4% SDS, 0.005% bromophenol blue, 10% glycerol) and analyzed by SDS-PAGE using 4–20% polyacrylamide gradient gels (Novex) under reducing conditions. The gel was stained with Coomassie Brilliant Blue. Lanes 1 and 6, 10 mg Mark-12 molecular weight markers (Novex, Inc.); lane 2, 50 mg total protein after addition of ammonium sulfate to concentrated CM (supernatant was dialyzed against PBS and subsequently loaded onto the gel); lane 3, 25 mg Phenyl Sepharose water eluate; lane 4, 10 mg Q Sepharose-purified rAFM; lane 5, 1 mg of Superdex 200-purified rAFM.

A single stable transfectant expressing high levels of AFM-specific mRNA was isolated. Immunoblots performed with AM339 (see Example 12) demonstrates that this antibody recognizes both rAFM produced from the transfectant as well as natural AFM isolated from human plasma (FIG. 5). rAFM was purified from CM derived from this transfectant (FIG. 6) and SDS-PAGE demonstrated rAFM to be greater than 95% pure with the same N-terminus as AFM purified from plasma (data not shown).

Example 8

Protein Purification

Serum-free CM was concentrated 10-fold and diafiltered against 25 mM sodium phosphate, pH 7.5 using a Filtron ultrafiltration apparatus loaded with 10K molecular weight cut-off filters. The CM was then adjusted with 3.9M ammonium sulfate to achieve a final ammonium sulfate concentration of 1.6M. This mixture was stirred for 0.5 hr; no precipitate was observed. The solution was then filtered in succession through 0.45 mm and 0.22 mm filters. The resultant filtrate was loaded onto a Phenyl Sepharose HP column previously equilibrated with 50 mM sodium phosphate, 1.6M ammonium sulfate; pH 7.5. Loading, washing and elution were done at a linear flow rate of 40 cm/hr. Following sample loading, the column was washed successively with 50 mM sodium phosphate, 1.6M ammonium sulfate, pH 7.5 and 50 mM sodium phosphate, pH 7.5. rAFM was eluted with water and detected by immunoblotting (see below).

The pH of the water eluate was adjusted to 8.0 with 0.1M Tris-base and loaded at a flow rate of 100 cm/hr onto a Q Sepharose HP column previously equilibrated with 20 mM Tris-HCl, pH 8.0. Following sample loading, the column was thoroughly washed with 20 mM Tris-HCl, pH 8.2, then with 0.1M NaCl, 20 mM Tris-HCl, pH 8.2. The column was then resolved with a 3 column volume (CV) linear gradient of NaCl ranging from 0–0.3M, followed by a 1 CV linear gradient of NaCl ranging from 0.3M to 1.0M in 20 mM Tris-HCl, pH 8.0. Fractions containing rAFM were pooled and loaded onto a Superdex 200 column previously equilibrated with phosphate-buffered saline pH 7.4. The column was loaded and resolved at a flow rate of 1 ml/min.

Example 9

Delipidation of AFM

To one volume of protein solution was added 2.5 volumes of 1-butano/diisopropyl ether (40:60). The mixture was shaken gently for 30 minutes at room temperature and then centrifuged for 5 minutes at 500 x g. The aqueous layer was recovered and to this was added a second 2.5 volumes of 1-butanol/diisopropyl ether (40:60). The sample was treated as before and the aqueous phase recovered. To the twice extracted aqueous phase was added one volume of diisopropyl ether, the mixture shaken and immediately centrifuged at 250 x g for 5 minutes. The aqueous layer was recovered and used as essentially delipidated.

Example 10

Immunoblotting

All samples for immunoblotting were electrophoresed on 4–20% SDS polyacylamide gels (Novex) and the proteins were then electrophoretically transferred to nitrocelluose membranes (Schleicher and Schuell, cat. no. BA83). The filters were first treated with polyclonal antibody AM339 that was raised in rabbits against a synthetic peptide (DLSLREGKFTDSENVC) (SEQ ID NO: 30) derived from amino acids 304–319 in AFM and then with donkey anti-rabbit Ig linked to horseradish peroxidase. Immune complexes were visualized by enhanced chemiluminescence according to the manufacturer's (Amersham) specifications.

Example 11

Nucleotide sequence comparisons

Nucleotide sequences were compared to the Genbank (Release 78.0) sequences using the method of Pearson and Lipman (Proc. Natl. Acad. Sci. USA 84, 2444–2448 (1988)) in the FASTA program of the Genetics Computer Group (GCG), Inc. (Madison, Wis.). Comparisons are shown in FIG. 2A.

Example 12

Generation of peptide antibodies specific for AFM

Since AFM was similar to at least three other members of the albumin family, it was possible that antibodies generated against the entire protein would also cross react with other albumin family proteins. To create AFM-specific antibodies, we first identified specific peptides of AFM which were dissimilar to peptide sequences found in the other albumin family proteins. These peptide sequences were then synthesized and the synthetic peptides were used to inject rabbits to obtain polyclonal antisera against each peptide. The AFM peptides that were synthesized are as follows:

| H1 | EKLVKDMVEYKDRC | (SEQ ID NO: 31) |
|---|---|---|
| | aa 43-56 in AFM | |
| The corresponding antibody is referred to as AM384. | | |
| H2 | CIINSNKDDRPKDLSLR | (SEQ ID NO: 32) |
| | aa 292-308 in AFM | |
| The corresponding antibody is referred to as AM 609. | | |
| H3 | DLSLREGKFTDSENVC | (SEQ ID NO: 30) |
| | aa 304-319 in AFM | |
| The corresponding antibody is referred to as AM 339. | | |
| H4 | CQERDADPDTFFAKFT | (SEQ ID NO: 33) |
| | aa 319-334 in AFM | |
| The corresponding antibody is referred to as AM 1104. | | |

Example 13

Generation of polyclonal antisera to AFM

Rabbit polyclonal antiserum was generated from purified AFM by methods that are standard in the art. The antiserum was found to bind specifically to AFM.
Discussion of Examples ALB family proteins are comprised of three homologous folding domains and are predicted to have evolved from an ancestral gene that coded for an approximately 190 amino acid single domain protein containing 3 double loops formed by 6 disulfide bridges. The genes in this family have all been mapped to the 4q11–q22 region of chromosome 4. AFM shares significant homology with ALB family proteins and has Cys residues consistent with a similar overall 3-domain organization. In addition, AFM has been localized to chromosome 4. Thus, there is compelling evidence that AFM is the fourth member of the ALB family.

There are some noteworthy distinctions among ALB family members. Concentrations in adult serum are 50 ng/ml for AFP, 350 mg/ml for VDB, 40 mg/ml for ALB and 30 mg/ml for AFM (data obtained by immunoblot analysis). ALB is not glycosylated, AFP and VDB each have 1 potential N-glycosylation site while AFM has 4 potential sites. ALB expresses one free thiol group that has been implicated in complex formation with Cys, glutathione, mercurial and gold compounds. In contrast, AFP and VDB have an even number of Cys residues and are thought not to have a free thiol. AFM has an even number of Cys residues, suggesting that it may not have a free thiol and may not bind glutathione and mercurials as does ALB.

There also are differences in the intradomain disulfide bonding pattern among ALB family members. VDB is predicted to have a disulfide bridge in double loop 1A. This bridge is absent in ALB, AFP and AFM. A disulfide bridge domain 2C is common to ALB, VDB and AFM but is not present in AFP. Thus, while the 4 ALB family proteins are evolutionarily related, there are clear differences in the molecular organization of these proteins.

Structural similarities between AFM and other ALB family members suggest that AFM could scavenge or transport a variety of ligands. We examined whether known ligand-binding sites in the sequence of ALB family proteins were also present in AFM. VDB has a binding site for sterols between amino acids 35–49 and a binding site for actin between amino acids 373–403. Using the GCG GAP program and the alignment of FIG. 2A, AFM has 60% similarity and 40% identity between VDB amino acids 35–49 but only 32% similarity and 10% identity between VDB amino acids 373–403. Thus, it is possible that AFM has sterol binding sites (e.g., the amino acids in AFM that correspond to amino acids 35–49 of VDB) but it is not likely to bind actin. The X-ray crystal structure of ALB was used to show that ALB binds a variety of ligands (aspirin, warfarin, IS, DIS, TIB, bilirubin) between amino acids 186–260 in domain 2A and an array of ligands (aspirin, diazepam, digitoxin, clofibrate, ibuprofen, IS, DIS, TIB, long chain fatty acids) between amino acids 379–455 in domain 3A. A GCG GAP comparison between analogous regions in AFM reveals that AFM has 54% similarity and 35% identity in domain 2A and 45% similarity and 25% identity in domain 3A. These moderate degrees of similarity make it possible but not conclusive as to whether AFM binds the same ligands as ALB in domains 2A and 3A.

Abbreviations

The abbreviations used in the above Examples are: AFM, afamin; AFP, a-fetoprotein; ALB, human serum albumin; CHO, Chinese Hamster Ovary; CM, conditioned medium; CV, column volume; DIS, 3, 5- diiodosalicyclic acid; DTT, dithiothreitol; HPLC, high performance liquid chromatography; IS, 5-iodosalicyclic acid; PAGE, polyacrylamide gel electrophoresis; PBS, phosphate-buffered saline; PCR, polymerase chain reaction; r, recombinant; TIB, 2,3,5- triioidobenzoic acid; VDP, vitamin D-binding protein.

The invention now being fully described, it will be apparent to one of ordinary skill in the art that many changes and modifications can be made thereto, without departing from the spirit and scope of the invention as set forth herein.

The embodiments of the invention in which an exclusive property or privilege is claimed are defined as follows:

1. A purified and isolated polynucleotide encoding amino acid residues 1 through 578 of SEQ. ID No.:2.

2. The purified and isolated polynucleotide of claim 1 comprising nucleotides 381 through 2114 of SEQ. ID. NO.:1.

3. A purified and isolated polynucleotide encoding amino acid residues −21 through 578 of SEQ. ID. NO.:2.

4. The purified and isolated polynucleotide of claim 3 comprising nucleotides 318 through 2114 of SEQ. ID. NO.:1.

5. A DNA sequence encoding a protein comprising amino acid residues 1 through 578 of SEQ. ID. NO.:2.

6. The DNA sequence of claim 5 comprising nucleotides 381 through 2114 of SEQ. ID. NO. :1.

7. The DNA sequence of claim 5 further comprising an endogenous control DNA sequence.

8. A host cell stably transformed or transfected with a DNA sequence according to claim 5.

9. A polynucleotide sequence complementary to a polynucleotide of claim 1 or 3.

10. A DNA vector comprising a DNA sequence of claim 5.

11. The vector of claim 10 further comprising an expression control DNA sequence.

12. A method of protein production, comprising the steps of:
  (a) culturing a host cell containing a polynucleotide encoding a protein comprising the amino acid sequence selected from 1 through 578 of SEQ. ID. NO.: 12 and −21 through 578 of SEQ. ID. NO.:2 under conditions suitable for the expression of said protein by said host cell; and
  (b) optionally, isolating said protein expressed by said host cell.

* * * * *

UNITED STATES PATENT AND TRADEMARK OFFICE
CERTIFICATE OF CORRECTION

PATENT NO. : 5,652,352
DATED : July 29, 1997
INVENTORS : Lichenstein et al.

It is certified that error appears in the above-identified patent and that said Letters Patent is hereby corrected as shown below:

Column 12, Line 34, delete "5".

Column 13, Line 54, change "are also are" to --are also--.

Column 17, Line 39, change "posible" to --possible--.

Column 20, Line 8, change "YVQSEQ ID NO: 6)" to --YVQ (SEQ ID NO: 6)--.

Column 21, Line 23, delete the second "to".

Line 62, change "the of AFM" to --the % similarity of AFM--.

Column 22, Line 45, change "GAA 5'" to --GAA+5'--.

Column 54, Line 53, change "12" to --2--.

Signed and Sealed this

Twenty-fourth Day of February, 1998

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 2287 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
        ( A ) NAME/KEY: CDS
        ( B ) LOCATION: 318..2117

( i x ) FEATURE:
        ( A ) NAME/KEY: mat_peptide
        ( B ) LOCATION: 381..2114

( i x ) FEATURE:
        ( A ) NAME/KEY: sig_peptide
        ( B ) LOCATION: 318..380

( x i ) SEQUENCE DESCRIPTION: SEQ ID NO:1:

```
CCCCGAGTCT   CTGCGCCTTC   ACATAGTTGT   CACAGGACTA   AAGCAAATTG   ATCCAGGGGG        60

AAACACTGTA   GACCGTGTAT   ATAAAAACAC   TCTATAAACT   GCAATGCTCA   ATTCTTAGTA       120

TAACTATTGT   TGTTGTATTG   ATATTTATTA   GTATTGGTGC   TCACAAAAAG   AGTCTAAATT       180

CCATAAGTCT   TTATATTCAG   GCTACTCTTT   ATTTTGAAA    ACTCATTTTC   TATCACCTTT       240

TTCTATTTTA   CTCCATATTG   AGGCCTCATA   AATCCAATTT   TTTATTTCTT   TCTTTTGTAA       300

ATGTGGTTTC   TACAAAG ATG AAA CTA CTA AAA CTT ACA GGT TTT ATT TTT               350
                    Met Lys Leu Leu Lys Leu Thr Gly Phe Ile Phe
                    -21 -20                      -15

TTC TTG TTT TTT TTG ACT GAA TCC CTA ACC CTG CCC ACA CAA CCT CGG                398
Phe Leu Phe Phe Leu Thr Glu Ser Leu Thr Leu Pro Thr Gln Pro Arg
-10            -5                   1                    5
```

-continued

| | | | | | | | | | | | | | | | | |
|---|---|---|---|---|---|---|---|---|---|---|---|---|---|---|---|---|
| GAT | ATA | GAG | AAC | TTC | AAT | AGT | ACT | CAA | AAA | TTT | ATA | GAA | GAT | AAT | ATT | 446 |
| Asp | Ile | Glu | Asn | Phe | Asn | Ser | Thr | Gln | Lys | Phe | Ile | Glu | Asp | Asn | Ile | |
| | 10 | | | | | | | 15 | | | | | 20 | | | |
| GAA | TAC | ATC | ACC | ATC | ATT | GCA | TTT | GCT | CAG | TAT | GTT | CAG | GAA | GCA | ACC | 494 |
| Glu | Tyr | Ile | Thr | Ile | Ile | Ala | Phe | Ala | Gln | Tyr | Val | Gln | Glu | Ala | Thr | |
| | | 25 | | | | | 30 | | | | | 35 | | | | |
| TTT | GAA | GAA | ATG | GAA | AAG | CTG | GTG | AAA | GAC | ATG | GTA | GAA | TAC | AAA | GAC | 542 |
| Phe | Glu | Glu | Met | Glu | Lys | Leu | Val | Lys | Asp | Met | Val | Glu | Tyr | Lys | Asp | |
| | 40 | | | | | 45 | | | | | 50 | | | | | |
| AGA | TGT | ATG | GCT | GAC | AAG | ACG | CTC | CCA | GAG | TGT | TCA | AAA | TTA | CCT | AAT | 590 |
| Arg | Cys | Met | Ala | Asp | Lys | Thr | Leu | Pro | Glu | Cys | Ser | Lys | Leu | Pro | Asn | |
| 55 | | | | | 60 | | | | | 65 | | | | | 70 | |
| AAT | GTT | TTA | CAG | GAA | AAA | ATA | TGT | GCT | ATG | GAG | GGG | CTG | CCA | CAA | AAG | 638 |
| Asn | Val | Leu | Gln | Glu | Lys | Ile | Cys | Ala | Met | Glu | Gly | Leu | Pro | Gln | Lys | |
| | | | | 75 | | | | | 80 | | | | | 85 | | |
| CAT | AAT | TTC | TCA | CAC | TGC | TGC | AGT | AAG | GTT | GAT | GCT | CAA | AGA | AGA | CTC | 686 |
| His | Asn | Phe | Ser | His | Cys | Cys | Ser | Lys | Val | Asp | Ala | Gln | Arg | Arg | Leu | |
| | | | 90 | | | | | 95 | | | | | 100 | | | |
| TGT | TTC | TTC | TAT | AAC | AAG | AAA | TCT | GAT | GTG | GGA | TTT | CTG | CCT | CCT | TTC | 734 |
| Cys | Phe | Phe | Tyr | Asn | Lys | Lys | Ser | Asp | Val | Gly | Phe | Leu | Pro | Pro | Phe | |
| | | 105 | | | | | 110 | | | | | 115 | | | | |
| CCT | ACC | CTG | GAT | CCC | GAA | GAG | AAA | TGC | CAG | GCT | TAT | GAA | AGT | AAC | AGA | 782 |
| Pro | Thr | Leu | Asp | Pro | Glu | Glu | Lys | Cys | Gln | Ala | Tyr | Glu | Ser | Asn | Arg | |
| 120 | | | | | 125 | | | | | 130 | | | | | | |
| GAA | TCC | CTT | TTA | AAT | CAC | TTT | TTA | TAT | GAA | GTT | GCC | AGA | AGG | AAC | CCA | 830 |
| Glu | Ser | Leu | Leu | Asn | His | Phe | Leu | Tyr | Glu | Val | Ala | Arg | Arg | Asn | Pro | |
| 135 | | | | | 140 | | | | | 145 | | | | | 150 | |
| TTT | GTC | TTC | GCC | CCT | ACA | CTT | CTA | ACT | GTT | GCT | GTT | CAT | TTT | GAG | GAG | 878 |
| Phe | Val | Phe | Ala | Pro | Thr | Leu | Leu | Thr | Val | Ala | Val | His | Phe | Glu | Glu | |
| | | | | 155 | | | | | 160 | | | | | 165 | | |
| GTG | GCC | AAA | TCA | TGT | TGT | GAA | GAA | CAA | AAC | AAA | GTC | AAC | TGC | CTT | CAA | 926 |
| Val | Ala | Lys | Ser | Cys | Cys | Glu | Glu | Gln | Asn | Lys | Val | Asn | Cys | Leu | Gln | |
| | | | 170 | | | | | 175 | | | | | 180 | | | |
| ACA | AGG | GCA | ATA | CCT | GTC | ACA | CAA | TAT | TTA | AAA | GCA | TTT | TCT | TCT | TAT | 974 |
| Thr | Arg | Ala | Ile | Pro | Val | Thr | Gln | Tyr | Leu | Lys | Ala | Phe | Ser | Ser | Tyr | |
| | | 185 | | | | | 190 | | | | | 195 | | | | |
| CAA | AAA | CAT | GTC | TGT | GGG | GCA | CTT | TTG | AAA | TTT | GGA | ACC | AAA | GTT | GTA | 1022 |
| Gln | Lys | His | Val | Cys | Gly | Ala | Leu | Leu | Lys | Phe | Gly | Thr | Lys | Val | Val | |
| | 200 | | | | 205 | | | | | 210 | | | | | | |
| CAC | TTT | ATA | TAT | ATT | GCG | ATA | CTC | AGT | CAA | AAA | TTC | CCC | AAG | ATT | GAA | 1070 |
| His | Phe | Ile | Tyr | Ile | Ala | Ile | Leu | Ser | Gln | Lys | Phe | Pro | Lys | Ile | Glu | |
| 215 | | | | | 220 | | | | | 225 | | | | | 230 | |
| TTT | AAG | GAG | CTT | ATT | TCT | CTT | GTA | GAA | GAT | GTT | TCT | TCC | AAC | TAT | GAT | 1118 |
| Phe | Lys | Glu | Leu | Ile | Ser | Leu | Val | Glu | Asp | Val | Ser | Ser | Asn | Tyr | Asp | |
| | | | | 235 | | | | | 240 | | | | | 245 | | |
| GGA | TGC | TGT | GAA | GGG | GAT | GTT | GTG | CAG | TGC | ATC | CGT | GAC | ACG | AGC | AAG | 1166 |
| Gly | Cys | Cys | Glu | Gly | Asp | Val | Val | Gln | Cys | Ile | Arg | Asp | Thr | Ser | Lys | |
| | | | 250 | | | | | 255 | | | | | 260 | | | |
| GTT | ATG | AAC | CAT | ATT | TGT | TCA | AAA | CAA | GAT | TCT | ATC | TCC | AGC | AAA | ATC | 1214 |
| Val | Met | Asn | His | Ile | Cys | Ser | Lys | Gln | Asp | Ser | Ile | Ser | Ser | Lys | Ile | |
| | | 265 | | | | | 270 | | | | | 275 | | | | |
| AAA | GAG | TGC | TGT | GAA | AAG | AAA | ATA | CCA | GAG | CGC | GGC | CAG | TGC | ATA | ATT | 1262 |
| Lys | Glu | Cys | Cys | Glu | Lys | Lys | Ile | Pro | Glu | Arg | Gly | Gln | Cys | Ile | Ile | |
| 280 | | | | | 285 | | | | | 290 | | | | | | |
| AAC | TCA | AAC | AAA | GAT | GAT | AGA | CCA | AAG | GAT | TTA | TCT | CTA | AGA | GAA | GGA | 1310 |
| Asn | Ser | Asn | Lys | Asp | Asp | Arg | Pro | Lys | Asp | Leu | Ser | Leu | Arg | Glu | Gly | |
| 295 | | | | 300 | | | | | 305 | | | | | 310 | | |
| AAA | TTT | ACT | GAC | AGT | GAA | AAT | GTG | TGT | CAA | GAA | CGA | GAT | GCT | GAC | CCA | 1358 |
| Lys | Phe | Thr | Asp | Ser | Glu | Asn | Val | Cys | Gln | Glu | Arg | Asp | Ala | Asp | Pro | |
| | | | | 315 | | | | | 320 | | | | | 325 | | |

```
GAC  ACC  TTC  TTT  GCG  AAG  TTT  ACT  TTT  GAA  TAC  TCA  AGG  AGA  CAT  CCA         1406
Asp  Thr  Phe  Phe  Ala  Lys  Phe  Thr  Phe  Glu  Tyr  Ser  Arg  Arg  His  Pro
               330                     335                     340

GAC  CTG  TCT  ATA  CCA  GAG  CTT  TTA  AGA  ATT  GTT  CAA  ATA  TAC  AAA  GAT         1454
Asp  Leu  Ser  Ile  Pro  Glu  Leu  Leu  Arg  Ile  Val  Gln  Ile  Tyr  Lys  Asp
               345                     350                     355

CTC  CTG  AGA  AAT  TGC  TGC  AAC  ACA  GAA  AAC  CCT  CCA  GGT  TGT  TAC  CGT         1502
Leu  Leu  Arg  Asn  Cys  Cys  Asn  Thr  Glu  Asn  Pro  Pro  Gly  Cys  Tyr  Arg
     360                     365                     370

TAC  GCG  GAA  GAC  AAA  TTC  AAT  GAG  ACA  ACT  GAG  AAA  AGC  CTC  AAG  ATG         1550
Tyr  Ala  Glu  Asp  Lys  Phe  Asn  Glu  Thr  Thr  Glu  Lys  Ser  Leu  Lys  Met
375                     380                     385                     390

GTA  CAA  CAA  GAA  TGT  AAA  CAT  TTC  CAG  AAT  TTG  GGG  AAG  GAT  GGT  TTG         1598
Val  Gln  Gln  Glu  Cys  Lys  His  Phe  Gln  Asn  Leu  Gly  Lys  Asp  Gly  Leu
                    395                     400                     405

AAA  TAC  CAT  TAC  CTC  ATC  AGG  CTC  ACG  AAG  ATA  GCT  CCC  CAA  CTC  TCC         1646
Lys  Tyr  His  Tyr  Leu  Ile  Arg  Leu  Thr  Lys  Ile  Ala  Pro  Gln  Leu  Ser
               410                     415                     420

ACT  GAA  GAA  CTG  GTG  TCT  CTT  GGC  GAG  AAA  ATG  GTG  ACA  GCT  TTC  ACT         1694
Thr  Glu  Glu  Leu  Val  Ser  Leu  Gly  Glu  Lys  Met  Val  Thr  Ala  Phe  Thr
          425                     430                     435

ACT  TGC  TGT  ACG  CTA  AGT  GAA  GAG  TTT  GCC  TGT  GTT  GAT  AAT  TTG  GCA         1742
Thr  Cys  Cys  Thr  Leu  Ser  Glu  Glu  Phe  Ala  Cys  Val  Asp  Asn  Leu  Ala
     440                     445                     450

GAT  TTA  GTT  TTT  GGA  GAG  TTA  TGT  GGA  GTA  AAT  GAA  AAT  CGA  ACT  ATC         1790
Asp  Leu  Val  Phe  Gly  Glu  Leu  Cys  Gly  Val  Asn  Glu  Asn  Arg  Thr  Ile
455                     460                     465                     470

AAC  CCT  GCT  GTG  GAC  CAC  TGC  TGT  AAA  ACA  AAC  TTT  GCC  TTC  AGA  AGG         1838
Asn  Pro  Ala  Val  Asp  His  Cys  Cys  Lys  Thr  Asn  Phe  Ala  Phe  Arg  Arg
               475                     480                     485

CCC  TGC  TTT  GAG  AGT  TTG  AAA  GCT  GAT  AAA  ACA  TAT  GTG  CCT  CCA  CCT         1886
Pro  Cys  Phe  Glu  Ser  Leu  Lys  Ala  Asp  Lys  Thr  Tyr  Val  Pro  Pro  Pro
          490                     495                     500

TTC  TCT  CAA  GAT  TTA  TTT  ACC  TTT  CAC  GCA  GAC  ATG  TGT  CAA  TCT  CAG         1934
Phe  Ser  Gln  Asp  Leu  Phe  Thr  Phe  His  Ala  Asp  Met  Cys  Gln  Ser  Gln
     505                     510                     515

AAT  GAG  GAG  CTT  CAG  AGG  AAG  ACA  GAC  AGG  TTT  CTT  GTC  AAC  TTA  GTG         1982
Asn  Glu  Glu  Leu  Gln  Arg  Lys  Thr  Asp  Arg  Phe  Leu  Val  Asn  Leu  Val
     520                     525                     530

AAG  CTG  AAG  CAT  GAA  CTC  ACA  GAT  GAA  GAG  CTG  CAG  TCT  TTG  TTT  ACA         2030
Lys  Leu  Lys  His  Glu  Leu  Thr  Asp  Glu  Glu  Leu  Gln  Ser  Leu  Phe  Thr
535                     540                     545                     550

AAT  TTC  GCA  AAT  GTA  GTG  GAT  AAG  TGC  TGC  AAA  GCA  GAG  AGT  CCT  GAA         2078
Asn  Phe  Ala  Asn  Val  Val  Asp  Lys  Cys  Cys  Lys  Ala  Glu  Ser  Pro  Glu
               555                     560                     565

GTC  TGC  TTT  AAT  GAA  GAG  AGT  CCA  AAA  ATT  GGC  AAC  TGAAGCCAGC                  2124
Val  Cys  Phe  Asn  Glu  Glu  Ser  Pro  Lys  Ile  Gly  Asn
          570                     575

TGCTGGAGAT  ATGTAAAGAA  AAAAGCACCA  AAGGGAAGGC  TTCCTATCTG  TGTGGTGATG                  2184

AATCGCATTT  CCTGAGAACA  AAATAAAAGG  ATTTTTCTGT  AACTGTCACC  TGAAATAATA                  2244

CATTGCAGCA  AGCAATAAAC  ACAACATTTT  GTAAAGTTAA  AAA                                     2287
```

( 2 ) INFORMATION FOR SEQ ID NO:2:

( i ) SEQUENCE CHARACTERISTICS:
        ( A ) LENGTH: 599 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Lys  Leu  Leu  Lys  Leu  Thr  Gly  Phe  Ile  Phe  Phe  Leu  Phe  Phe  Leu
-21  -20            -15                      -10

Thr  Glu  Ser  Leu  Thr  Leu  Pro  Thr  Gln  Pro  Arg  Asp  Ile  Glu  Asn  Phe
 -5                        1                   5                          10

Asn  Ser  Thr  Gln  Lys  Phe  Ile  Glu  Asp  Asn  Ile  Glu  Tyr  Ile  Thr  Ile
               15                       20                        25

Ile  Ala  Phe  Ala  Gln  Tyr  Val  Gln  Glu  Ala  Thr  Phe  Glu  Glu  Met  Glu
          30                        35                        40

Lys  Leu  Val  Lys  Asp  Met  Val  Glu  Tyr  Lys  Asp  Arg  Cys  Met  Ala  Asp
     45                  50                         55

Lys  Thr  Leu  Pro  Glu  Cys  Ser  Lys  Leu  Pro  Asn  Asn  Val  Leu  Gln  Glu
60                       65                       70                        75

Lys  Ile  Cys  Ala  Met  Glu  Gly  Leu  Pro  Gln  Lys  His  Asn  Phe  Ser  His
                    80                       85                         90

Cys  Cys  Ser  Lys  Val  Asp  Ala  Gln  Arg  Arg  Leu  Cys  Phe  Phe  Tyr  Asn
               95                       100                       105

Lys  Lys  Ser  Asp  Val  Gly  Phe  Leu  Pro  Pro  Phe  Pro  Thr  Leu  Asp  Pro
          110                      115                       120

Glu  Glu  Lys  Cys  Gln  Ala  Tyr  Glu  Ser  Asn  Arg  Glu  Ser  Leu  Leu  Asn
     125                      130                      135

His  Phe  Leu  Tyr  Glu  Val  Ala  Arg  Arg  Asn  Pro  Phe  Val  Phe  Ala  Pro
140                      145                      150                       155

Thr  Leu  Leu  Thr  Val  Ala  Val  His  Phe  Glu  Glu  Val  Ala  Lys  Ser  Cys
                    160                      165                      170

Cys  Glu  Glu  Gln  Asn  Lys  Val  Asn  Cys  Leu  Gln  Thr  Arg  Ala  Ile  Pro
               175                      180                      185

Val  Thr  Gln  Tyr  Leu  Lys  Ala  Phe  Ser  Ser  Tyr  Gln  Lys  His  Val  Cys
          190                      195                      200

Gly  Ala  Leu  Leu  Lys  Phe  Gly  Thr  Lys  Val  Val  His  Phe  Ile  Tyr  Ile
     205                      210                      215

Ala  Ile  Leu  Ser  Gln  Lys  Phe  Pro  Lys  Ile  Glu  Phe  Lys  Glu  Leu  Ile
220                      225                      230                       235

Ser  Leu  Val  Glu  Asp  Val  Ser  Ser  Asn  Tyr  Asp  Gly  Cys  Cys  Glu  Gly
                    240                      245                      250

Asp  Val  Val  Gln  Cys  Ile  Arg  Asp  Thr  Ser  Lys  Val  Met  Asn  His  Ile
               255                      260                      265

Cys  Ser  Lys  Gln  Asp  Ser  Ile  Ser  Ser  Lys  Ile  Lys  Glu  Cys  Cys  Glu
          270                      275                      280

Lys  Lys  Ile  Pro  Glu  Arg  Gly  Gln  Cys  Ile  Ile  Asn  Ser  Asn  Lys  Asp
     285                      290                      295

Asp  Arg  Pro  Lys  Asp  Leu  Ser  Leu  Arg  Glu  Gly  Lys  Phe  Thr  Asp  Ser
300                      305                      310                       315

Glu  Asn  Val  Cys  Gln  Glu  Arg  Asp  Ala  Asp  Pro  Asp  Thr  Phe  Phe  Ala
               320                      325                      330

Lys  Phe  Thr  Phe  Glu  Tyr  Ser  Arg  Arg  His  Pro  Asp  Leu  Ser  Ile  Pro
               335                      340                      345

Glu  Leu  Leu  Arg  Ile  Val  Gln  Ile  Tyr  Lys  Asp  Leu  Leu  Arg  Asn  Cys
          350                      355                      360

Cys  Asn  Thr  Glu  Asn  Pro  Pro  Gly  Cys  Tyr  Arg  Tyr  Ala  Glu  Asp  Lys
     365                      370                      375

Phe  Asn  Glu  Thr  Thr  Glu  Lys  Ser  Leu  Lys  Met  Val  Gln  Gln  Glu  Cys
380                      385                      390                       395
```

| Lys | His | Phe | Gln | Asn | Leu | Gly | Lys | Asp | Gly | Leu | Lys | Tyr | His | Tyr | Leu |
|-----|-----|-----|-----|-----|-----|-----|-----|-----|-----|-----|-----|-----|-----|-----|-----|
|     |     |     |     | 400 |     |     |     | 405 |     |     |     |     |     | 410 |     |
| Ile | Arg | Leu | Thr | Lys | Ile | Ala | Pro | Gln | Leu | Ser | Thr | Glu | Glu | Leu | Val |
|     |     |     | 415 |     |     |     |     | 420 |     |     |     | 425 |     |     |     |
| Ser | Leu | Gly | Glu | Lys | Met | Val | Thr | Ala | Phe | Thr | Thr | Cys | Cys | Thr | Leu |
|     |     | 430 |     |     |     | 435 |     |     |     |     |     | 440 |     |     |     |
| Ser | Glu | Glu | Phe | Ala | Cys | Val | Asp | Asn | Leu | Ala | Asp | Leu | Val | Phe | Gly |
|     | 445 |     |     |     |     | 450 |     |     |     |     | 455 |     |     |     |     |
| Glu | Leu | Cys | Gly | Val | Asn | Glu | Asn | Arg | Thr | Ile | Asn | Pro | Ala | Val | Asp |
| 460 |     |     |     |     | 465 |     |     |     |     | 470 |     |     |     |     | 475 |
| His | Cys | Cys | Lys | Thr | Asn | Phe | Ala | Phe | Arg | Arg | Pro | Cys | Phe | Glu | Ser |
|     |     |     |     | 480 |     |     |     |     | 485 |     |     |     |     | 490 |     |
| Leu | Lys | Ala | Asp | Lys | Thr | Tyr | Val | Pro | Pro | Pro | Phe | Ser | Gln | Asp | Leu |
|     |     |     | 495 |     |     |     |     | 500 |     |     |     |     | 505 |     |     |
| Phe | Thr | Phe | His | Ala | Asp | Met | Cys | Gln | Ser | Gln | Asn | Glu | Glu | Leu | Gln |
|     |     | 510 |     |     |     |     | 515 |     |     |     |     | 520 |     |     |     |
| Arg | Lys | Thr | Asp | Arg | Phe | Leu | Val | Asn | Leu | Val | Lys | Leu | Lys | His | Glu |
|     | 525 |     |     |     |     | 530 |     |     |     |     | 535 |     |     |     |     |
| Leu | Thr | Asp | Glu | Glu | Leu | Gln | Ser | Leu | Phe | Thr | Asn | Phe | Ala | Asn | Val |
| 540 |     |     |     |     | 545 |     |     |     |     | 550 |     |     |     |     | 555 |
| Val | Asp | Lys | Cys | Cys | Lys | Ala | Glu | Ser | Pro | Glu | Val | Cys | Phe | Asn | Glu |
|     |     |     |     | 560 |     |     |     |     | 565 |     |     |     |     | 570 |     |
| Glu | Ser | Pro | Lys | Ile | Gly | Asn |
|     |     |     | 575 |     |     |     |

(2) INFORMATION FOR SEQ ID NO:3:

(i) SEQUENCE CHARACTERISTICS:
        (A) LENGTH: 609 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:3:

| Met | Lys | Trp | Val | Thr | Phe | Ile | Ser | Leu | Leu | Phe | Leu | Phe | Ser | Ser | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Tyr | Ser | Arg | Gly | Val | Phe | Arg | Arg | Asp | Ala | His | Lys | Ser | Glu | Val | Ala |
|     |     |     | 20  |     |     |     |     | 25  |     |     |     |     | 30  |     |     |
| His | Arg | Phe | Lys | Asp | Leu | Gly | Glu | Glu | Asn | Phe | Lys | Ala | Leu | Val | Leu |
|     |     | 35  |     |     |     |     | 40  |     |     |     |     | 45  |     |     |     |
| Ile | Ala | Phe | Ala | Gln | Tyr | Leu | Gln | Gln | Cys | Pro | Phe | Glu | Asp | His | Val |
|     | 50  |     |     |     |     | 55  |     |     |     |     | 60  |     |     |     |     |
| Lys | Leu | Val | Asn | Glu | Val | Thr | Glu | Phe | Ala | Lys | Thr | Cys | Val | Ala | Asp |
| 65  |     |     |     |     | 70  |     |     |     |     | 75  |     |     |     |     | 80  |
| Glu | Ser | Ala | Glu | Asn | Cys | Asp | Lys | Ser | Leu | His | Thr | Leu | Phe | Gly | Asp |
|     |     |     |     | 85  |     |     |     |     | 90  |     |     |     |     | 95  |     |
| Lys | Leu | Cys | Thr | Val | Ala | Thr | Leu | Arg | Glu | Thr | Tyr | Gly | Glu | Met | Ala |
|     |     |     |     | 100 |     |     |     |     | 105 |     |     |     |     | 110 |     |
| Asp | Cys | Cys | Ala | Lys | Gln | Glu | Pro | Glu | Arg | Asn | Glu | Cys | Phe | Leu | Gln |
|     |     | 115 |     |     |     |     | 120 |     |     |     |     | 125 |     |     |     |
| His | Lys | Asp | Asp | Asn | Pro | Asn | Leu | Pro | Arg | Leu | Val | Arg | Pro | Glu | Val |
|     | 130 |     |     |     |     | 135 |     |     |     |     | 140 |     |     |     |     |
| Asp | Val | Met | Cys | Thr | Ala | Phe | His | Asp | Asn | Glu | Glu | Thr | Phe | Leu | Lys |
| 145 |     |     |     |     | 150 |     |     |     |     | 155 |     |     |     |     | 160 |

| | | | | | | | | | | | | | | |
|---|---|---|---|---|---|---|---|---|---|---|---|---|---|---|
|Lys|Tyr|Leu|Tyr|Glu|Ile|Ala|Arg|Arg|His|Pro|Tyr|Phe|Tyr|Ala|Pro|
| | | | |165| | | |170| | | |175| | |
|Glu|Leu|Leu|Phe|Phe|Ala|Lys|Arg|Tyr|Lys|Ala|Ala|Phe|Thr|Glu|Cys|
| | | |180| | | |185| | | |190| | | |
|Cys|Gln|Ala|Ala|Asp|Lys|Ala|Ala|Cys|Leu|Leu|Pro|Lys|Leu|Asp|Glu|
| | |195| | | |200| | | |205| | | | |
|Leu|Arg|Asp|Glu|Gly|Lys|Ala|Ser|Ser|Ala|Lys|Gln|Arg|Leu|Lys|Cys|
| |210| | | |215| | | |220| | | | | |
|Ala|Ser|Leu|Gln|Lys|Phe|Gly|Glu|Arg|Ala|Phe|Lys|Ala|Trp|Ala|Val|
|225| | | |230| | | |235| | | | | |240|
|Ala|Arg|Leu|Ser|Gln|Arg|Phe|Pro|Lys|Ala|Glu|Phe|Ala|Glu|Val|Ser|
| | | |245| | | |250| | | |255| | | |
|Lys|Leu|Val|Thr|Asp|Leu|Thr|Lys|Val|His|Thr|Glu|Cys|Cys|His|Gly|
| | |260| | | |265| | | |270| | | | |
|Asp|Leu|Leu|Glu|Cys|Ala|Asp|Asp|Arg|Ala|Asp|Leu|Ala|Lys|Tyr|Ile|
| |275| | | |280| | | |285| | | | | |
|Cys|Glu|Asn|Gln|Asp|Ser|Ile|Ser|Ser|Lys|Leu|Lys|Glu|Cys|Cys|Glu|
|290| | | |295| | | |300| | | | | | |
|Lys|Pro|Leu|Leu|Glu|Lys|Ser|His|Cys|Ile|Ala|Glu|Val|Glu|Asn|Asp|
|305| | | |310| | | |315| | | | | |320|
|Glu|Met|Pro|Ala|Asp|Leu|Pro|Ser|Leu|Ala|Ala|Asp|Phe|Val|Glu|Ser|
| | | |325| | | |330| | | |335| | | |
|Lys|Asp|Val|Cys|Lys|Asn|Tyr|Ala|Glu|Ala|Lys|Asp|Val|Phe|Leu|Gly|
| | |340| | | |345| | | |350| | | | |
|Met|Phe|Leu|Tyr|Glu|Tyr|Ala|Arg|Arg|His|Pro|Asp|Tyr|Ser|Val|Val|
| |355| | | |360| | | |365| | | | | |
|Leu|Leu|Leu|Arg|Leu|Ala|Lys|Thr|Tyr|Glu|Thr|Thr|Leu|Glu|Lys|Cys|
|370| | | |375| | | |380| | | | | | |
|Cys|Ala|Ala|Ala|Asp|Pro|His|Glu|Cys|Tyr|Ala|Lys|Val|Phe|Asp|Glu|
|385| | | |390| | | |395| | | | | |400|
|Phe|Lys|Pro|Leu|Val|Glu|Glu|Pro|Gln|Asn|Leu|Ile|Lys|Gln|Asn|Cys|
| | | |405| | | |410| | | |415| | | |
|Glu|Leu|Phe|Lys|Gln|Leu|Gly|Glu|Tyr|Lys|Phe|Gln|Asn|Ala|Leu|Leu|
| | |420| | | |425| | | |430| | | | |
|Val|Arg|Tyr|Thr|Lys|Lys|Val|Pro|Gln|Val|Ser|Thr|Pro|Thr|Leu|Val|
| |435| | | |440| | | |445| | | | | |
|Glu|Val|Ser|Arg|Asn|Leu|Gly|Lys|Val|Gly|Ser|Lys|Cys|Cys|Lys|His|
|450| | | |455| | | |460| | | | | | |
|Pro|Glu|Ala|Lys|Arg|Met|Pro|Cys|Ala|Glu|Asp|Tyr|Leu|Ser|Val|Val|
|465| | | |470| | | |475| | | | | |480|
|Leu|Asn|Gln|Leu|Cys|Val|Leu|His|Glu|Lys|Thr|Pro|Val|Ser|Asp|Arg|
| | | |485| | | |490| | | |495| | | |
|Val|Thr|Lys|Cys|Cys|Thr|Glu|Ser|Leu|Val|Asn|Arg|Arg|Pro|Cys|Phe|
| | |500| | | |505| | | |510| | | | |
|Ser|Ala|Leu|Glu|Val|Asp|Glu|Thr|Tyr|Val|Pro|Lys|Glu|Phe|Asn|Ala|
| |515| | | |520| | | |525| | | | | |
|Glu|Thr|Phe|Thr|Phe|His|Ala|Asp|Ile|Cys|Thr|Leu|Ser|Glu|Lys|Glu|
| |530| | | |535| | | |540| | | | | |
|Arg|Gln|Ile|Lys|Lys|Gln|Thr|Ala|Leu|Val|Glu|Leu|Val|Lys|His|Lys|
|545| | | |550| | | |555| | | | | |560|
|Pro|Lys|Ala|Thr|Lys|Glu|Gln|Leu|Lys|Ala|Val|Met|Asp|Asp|Phe|Ala|
| | | |565| | | |570| | | |575| | | |
|Ala|Phe|Val|Glu|Lys|Cys|Cys|Lys|Ala|Asp|Asp|Lys|Glu|Thr|Cys|Phe|
| | |580| | | |585| | | |590| | | | |

-continued

```
Ala Glu Glu Gly Lys Lys Leu Val Ala Ala Ser Gln Ala Ala Leu Gly
        595                 600                 605

Leu
```

( 2 ) INFORMATION FOR SEQ ID NO:4:

( i ) SEQUENCE CHARACTERISTICS:
    ( A ) LENGTH: 609 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:4:

```
Met Lys Trp Val Glu Ser Ile Phe Leu Ile Phe Leu Leu Asn Phe Thr
 1               5                  10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
    130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
    210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
        275                 280                 285

Cys Ser Gln Gln Asp Thr Leu Ser Asn Lys Ile Thr Glu Cys Cys Lys
    290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
```

325                              330                              335

Arg   Asp   Phe   Asn   Gln   Phe   Ser   Ser   Gly   Glu   Lys   Asn   Ile   Phe   Leu   Ala
                           340                             345                       350

Ser   Phe   Val   His   Glu   Tyr   Ser   Arg   His   Pro   Gln   Leu   Ala   Val   Ser
                     355                             360                       365

Val   Ile   Leu   Arg   Val   Ala   Lys   Gly   Tyr   Gln   Glu   Leu   Leu   Glu   Lys   Cys
                     370                             375                       380

Phe   Gln   Thr   Glu   Asn   Pro   Leu   Glu   Cys   Gln   Asp   Lys   Gly   Glu   Glu   Glu
         385                             390                             395                             400

Leu   Gln   Lys   Tyr   Ile   Gln   Glu   Ser   Gln   Ala   Leu   Ala   Lys   Arg   Ser   Cys
                                 405                             410                       415

Gly   Leu   Phe   Gln   Lys   Leu   Gly   Glu   Tyr   Tyr   Leu   Gln   Asn   Ala   Phe   Leu
                           420                             425                       430

Val   Ala   Tyr   Thr   Lys   Lys   Ala   Pro   Gln   Leu   Thr   Ser   Ser   Glu   Leu   Met
                     435                             440                       445

Ala   Ile   Thr   Arg   Lys   Met   Ala   Ala   Thr   Ala   Ala   Thr   Cys   Cys   Gln   Leu
                     450                             455                       460

Ser   Glu   Asp   Lys   Leu   Leu   Ala   Cys   Gly   Glu   Gly   Ala   Ala   Asp   Ile   Ile
         465                             470                             475                             480

Ile   Gly   His   Leu   Cys   Ile   Arg   His   Glu   Met   Thr   Pro   Val   Asn   Pro   Gly
                           485                             490                       495

Val   Gly   Gln   Cys   Cys   Thr   Ser   Ser   Tyr   Ala   Asn   Arg   Arg   Pro   Cys   Phe
                           500                             505                       510

Ser   Ser   Leu   Val   Val   Asp   Glu   Thr   Tyr   Val   Pro   Pro   Ala   Phe   Ser   Asp
                     515                             520                       525

Asp   Lys   Phe   Ile   Phe   His   Lys   Asp   Leu   Cys   Gln   Ala   Gln   Gly   Val   Ala
                     530                             535                       540

Leu   Gln   Thr   Met   Lys   Gln   Glu   Phe   Leu   Ile   Asn   Leu   Val   Lys   Gln   Lys
         545                             550                             555                             560

Pro   Gln   Ile   Thr   Glu   Glu   Gln   Leu   Glu   Ala   Val   Ile   Ala   Asp   Phe   Ser
                           565                             570                       575

Gly   Leu   Leu   Glu   Lys   Cys   Cys   Gln   Gly   Gln   Glu   Gln   Val   Cys   Phe
                           580                             585                       590

Ala   Glu   Glu   Gly   Gln   Lys   Leu   Ile   Ser   Lys   Thr   Arg   Ala   Ala   Leu   Gly
                     595                             600                       605

Val ( 2 ) INFORMATION FOR SEQ ID NO:5:

( i ) SEQUENCE CHARACTERISTICS:
        ( A ) LENGTH: 474 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:5:

Met   Lys   Arg   Val   Leu   Val   Leu   Leu   Leu   Ala   Val   Ala   Phe   Gly   His   Ala
         1                 5                             10                            15

Leu   Glu   Arg   Gly   Arg   Asp   Tyr   Glu   Lys   Asn   Lys   Val   Cys   Lys   Glu   Phe
                     20                            25                             30

Ser   His   Leu   Gly   Lys   Glu   Asp   Phe   Thr   Ser   Leu   Ser   Leu   Val   Leu   Tyr
                     35                            40                             45

Ser   Arg   Lys   Phe   Pro   Ser   Gly   Thr   Phe   Glu   Gln   Val   Ser   Gln   Leu   Val
                     50                            55                             60

-continued

| | | | | | | | | | | | | | | | |
|---|---|---|---|---|---|---|---|---|---|---|---|---|---|---|---|
| Lys<br>65 | Glu | Val | Val | Ser | Leu<br>70 | Thr | Glu | Ala | Cys<br>75 | Cys | Ala | Glu | Gly | Ala | Asp<br>80 |
| Pro | Asp | Cys | Tyr | Asp<br>85 | Thr | Arg | Thr | Ser | Ala<br>90 | Leu | Ser | Ala | Lys | Ser<br>95 | Cys |
| Glu | Ser | Asn | Ser<br>100 | Pro | Phe | Pro | Val | His<br>105 | Pro | Gly | Thr | Ala | Glu<br>110 | Cys | Cys |
| Thr | Lys | Glu<br>115 | Gly | Leu | Glu | Arg | Lys<br>120 | Leu | Cys | Met | Ala | Ala<br>125 | Leu | Lys | His |
| Gln | Pro<br>130 | Gln | Glu | Phe | Pro | Thr<br>135 | Tyr | Val | Glu | Pro | Thr<br>140 | Asn | Asp | Glu | Ile |
| Cys<br>145 | Glu | Ala | Phe | Arg | Lys<br>150 | Asp | Pro | Lys | Glu | Tyr<br>155 | Ala | Asn | Gln | Phe | Met<br>160 |
| Trp | Glu | Tyr | Ser | Thr<br>165 | Asn | Tyr | Gly | Gln | Ala<br>170 | Pro | Leu | Ser | Leu<br>175 | Leu | Val |
| Ser | Tyr | Thr | Lys<br>180 | Ser | Tyr | Leu | Ser | Met<br>185 | Val | Gly | Ser | Cys<br>190 | Cys | Thr | Ser |
| Ala | Ser | Pro<br>195 | Thr | Val | Cys | Phe | Leu<br>200 | Lys | Glu | Arg | Leu<br>205 | Gln | Leu | Lys | His |
| Leu | Ser<br>210 | Leu | Leu | Thr | Thr | Leu<br>215 | Ser | Asn | Arg | Val | Cys<br>220 | Ser | Gln | Tyr | Ala |
| Ala<br>225 | Tyr | Gly | Glu | Lys | Lys<br>230 | Ser | Arg | Leu | Ser | Asn<br>235 | Leu | Ile | Lys | Leu | Ala<br>240 |
| Gln | Lys | Val | Pro | Thr<br>245 | Ala | Asp | Leu | Glu | Asp<br>250 | Val | Leu | Pro | Leu | Ala<br>255 | Glu |
| Asp | Ile | Thr | Asn | Ile<br>260 | Leu | Ser | Lys | Cys | Cys<br>265 | Glu | Ser | Ala | Ser | Glu<br>270 | Asp |
| Cys | Met | Ala<br>275 | Lys | Glu | Leu | Pro | Glu<br>280 | His | Thr | Val | Lys | Leu<br>285 | Cys | Asp | Asn |
| Leu | Ser<br>290 | Thr | Lys | Asn | Ser | Lys<br>295 | Phe | Glu | Asp | Cys | Cys<br>300 | Gln | Glu | Lys | Thr |
| Ala<br>305 | Met | Asp | Val | Phe | Val<br>310 | Cys | Thr | Tyr | Phe | Met<br>315 | Pro | Ala | Ala | Gln | Leu<br>320 |
| Pro | Glu | Leu | Pro | Asp<br>325 | Val | Glu | Leu | Pro | Thr<br>330 | Asn | Lys | Asp | Val | Cys<br>335 | Asp |
| Pro | Gly | Asn | Thr<br>340 | Lys | Val | Met | Asp | Lys<br>345 | Tyr | Thr | Phe | Glu | Leu<br>350 | Ser | Arg |
| Arg | Thr | His<br>355 | Leu | Pro | Glu | Val | Phe<br>360 | Leu | Ser | Lys | Val | Leu<br>365 | Glu | Pro | Thr |
| Leu | Lys<br>370 | Ser | Leu | Gly | Glu | Cys<br>375 | Cys | Asp | Val | Glu | Asp<br>380 | Ser | Thr | Thr | Cys |
| Phe<br>385 | Asn | Ala | Lys | Gly | Pro<br>390 | Leu | Leu | Lys | Lys | Glu<br>395 | Leu | Ser | Ser | Phe | Ile<br>400 |
| Asp | Lys | Gly | Gln | Glu<br>405 | Leu | Cys | Ala | Asp | Tyr<br>410 | Ser | Glu | Asn | Thr | Phe<br>415 | Thr |
| Glu | Tyr | Lys | Lys<br>420 | Lys | Leu | Ala | Glu | Arg<br>425 | Leu | Lys | Ala | Lys | Leu<br>430 | Pro | Asp |
| Ala | Thr | Pro<br>435 | Lys | Glu | Leu | Ala | Lys<br>440 | Leu | Val | Asn | Lys | Arg<br>445 | Ser | Asp | Phe |
| Ala | Ser<br>450 | Asn | Cys | Cys | Ser | Ile<br>455 | Asn | Ser | Pro | Pro | Leu<br>460 | Tyr | Cys | Asp | Ser |
| Glu<br>465 | Ile | Asp | Ala | Glu | Leu<br>470 | Lys | Asn | Ile | Leu | | | | | | |

( 2 ) INFORMATION FOR SEQ ID NO:6:

( i ) SEQUENCE CHARACTERISTICS:
   ( A ) LENGTH: 35 amino acids
   ( B ) TYPE: amino acid
   ( C ) STRANDEDNESS: unknown
   ( D ) TOPOLOGY: unknown ( i i ) MOLECULE TYPE: peptide ( x i ) SEQUENCE DESCRIPTION: SEQ ID NO:6:

```
Leu Pro Thr Gln Pro Arg Asp Ile Glu Asn Phe Xaa Ser Thr Gln Lys
1               5                   10                  15

Phe Ile Glu Asp Asn Ile Glu Tyr Ile Thr Ile Ile Ala Phe Ala Gln
            20                  25                  30

Tyr Val Gln
        35
```

( 2 ) INFORMATION FOR SEQ ID NO:7:

( i ) SEQUENCE CHARACTERISTICS:
      ( A ) LENGTH: 6 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:7:

```
Tyr His Tyr Leu Ile Arg
1               5
```

( 2 ) INFORMATION FOR SEQ ID NO:8:

( i ) SEQUENCE CHARACTERISTICS:
      ( A ) LENGTH: 7 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:8:

```
Phe Thr Phe Glu Tyr Ser Arg
1               5
```

( 2 ) INFORMATION FOR SEQ ID NO:9:

( i ) SEQUENCE CHARACTERISTICS:
      ( A ) LENGTH: 15 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:9:

```
Phe Thr Asp Ser Glu Asn Val Cys Gln Glu Arg Asp Ala Asp Pro
1               5                   10                  15
```

( 2 ) INFORMATION FOR SEQ ID NO:10:

( i ) SEQUENCE CHARACTERISTICS:
      ( A ) LENGTH: 10 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:10:

```
     Ile  Val  Gln  Ile  Tyr  Lys  Asp  Leu  Leu  Arg
     1                 5                         10
```

( 2 ) INFORMATION FOR SEQ ID NO:11:

( i ) SEQUENCE CHARACTERISTICS:
        ( A ) LENGTH: 15 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:11:

```
     Ile  Ala  Pro  Gln  Leu  Ser  Thr  Glu  Glu  Leu  Val  Ser  Leu  Gly  Glu
     1                 5                         10                        15
```

( 2 ) INFORMATION FOR SEQ ID NO:12:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:12:

```
     Arg  His  Pro  Asp  Leu  Ser  Ile  Pro  Glu  Leu  Leu  Arg
     1                 5                         10
```

( 2 ) INFORMATION FOR SEQ ID NO:13:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:13:

```
     Glu  Ser  Leu  Leu  Asn  His  Phe  Leu  Tyr  Glu  Val  Ala  Arg
     1                 5                         10
```

( 2 ) INFORMATION FOR SEQ ID NO:14:

( i ) SEQUENCE CHARACTERISTICS:
        ( A ) LENGTH: 25 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:14:

```
     Arg  Asn  Pro  Phe  Val  Phe  Ala  Pro  Thr  Leu  Leu  Thr  Val  Ala  Val  His
     1                 5                         10                        15

Phe  Glu  Glu  Val  Ala  Lys  Ser  Cys  Cys
                      20                    25
```

( 2 ) INFORMATION FOR SEQ ID NO:15:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:15:

Gln Lys Phe Ile Glu Asp Asn
1               5

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:16:

ACGCTGAATT CGCCARAART TYATHGARGA YAA              33

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:17:

Ile Val Gln Ile Tyr Lys Asp
1               5

( 2 ) INFORMATION FOR SEQ ID NO:18:

( i ) SEQUENCE CHARACTERISTICS:
        ( A ) LENGTH: 34 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:18:

ACGCTAAGCT TGCRTCYTTR TADATYTGNA CDAT          34

( 2 ) INFORMATION FOR SEQ ID NO:19:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:19:

Asp Asn Ile Glu Tyr Ile Thr
1               5

( 2 ) INFORMATION FOR SEQ ID NO:20:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:20:

ACGCTGAATT CGCGA Y AA Y A THGAR-
TA Y AT HAC                                                          33

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:21:

Phe  Thr  Phe  Glu  Tyr  Ser
  1                        5

( 2 ) INFORMATION FOR SEQ ID NO:22:

( i ) SEQUENCE CHARACTERISTICS:
        ( A ) LENGTH: 31 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:22:

ACGCTAAGCT TGCNGARTA Y TCRAANGTRA A                                  31

( 2 ) INFORMATION FOR SEQ ID NO:23:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:23:

TATGTGCTAT GGAGGGGC                                                  18

( 2 ) INFORMATION FOR SEQ ID NO:24:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:24:

CAACCCTGCT GTGGACCA                                                  18

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:25:

GCACATATGT TTTATCAGCT TT                                             22

( 2 ) INFORMATION FOR SEQ ID NO:26:

( i ) SEQUENCE CHARACTERISTICS:
        ( A ) LENGTH: 38 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:26:

TCACCTCTAG ACCACCATGA AACTACTAAA ACTTACAG         38

( 2 ) INFORMATION FOR SEQ ID NO:27:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:27:

AATTTCTCAG GAGATCTTTG TATA         24

( 2 ) INFORMATION FOR SEQ ID NO:28:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:28:

AAATATACAA AGATCTCCTG AGAA         24

( 2 ) INFORMATION FOR SEQ ID NO:29:

( i ) SEQUENCE CHARACTERISTICS:
        ( A ) LENGTH: 31 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:29:

TCCCGGTCGA CTCAGTTGCC AATTTTGGA C         31

( 2 ) INFORMATION FOR SEQ ID NO:30:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:30:

Asp Leu Ser Leu Arg Glu Gly Lys Phe Thr Asp Ser Glu Asn Val Cys
    1              5                    10                15

( 2 ) INFORMATION FOR SEQ ID NO:31:

(i) SEQUENCE CHARACTERISTICS:
  (A) LENGTH: 14 amino acids
  (B) TYPE: amino acid
  (C) STRANDEDNESS: unknown
  (D) TOPOLOGY: unknown (ii) MOLECULE TYPE: peptide (xi) SEQUENCE DESCRIPTION: SEQ ID NO:31:

```
Glu Lys Leu Val Lys Asp Met Val Glu Tyr Lys Asp Arg Cys
 1               5                  10
```

(2) INFORMATION FOR SEQ ID NO:32:

(i) SEQUENCE CHARACTERISTICS:
    (A) LENGTH: 17 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:32:

```
Cys Ile Ile Asn Ser Asn Lys Asp Asp Arg Pro Lys Asp Leu Ser Leu
 1               5                  10                  15
Arg
```

(2) INFORMATION FOR SEQ ID NO:33:

(i) SEQUENCE CHARACTERISTICS:
    (A) LENGTH: 16 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:33:

```
Cys Gln Glu Arg Asp Ala Asp Pro Asp Thr Phe Phe Ala Lys Phe Thr
 1               5                  10                  15
```